United States Patent
Staecker et al.

(10) Patent No.: US 12,391,936 B2
(45) Date of Patent: *Aug. 19, 2025

(54) GENE THERAPY SYSTEMS AND RELATED METHODS FOR TREATMENT OF HEARING LOSS

(71) Applicant: RESCUE HEARING INC., Gainesville, FL (US)

(72) Inventors: Hinrich Staecker, Leawood, KS (US); Caesar James Ayala, Gainesville, FL (US)

(73) Assignee: Rescue Hearing, Inc., Gainesville, FL (US)

( * ) Notice: Subject to any disclaimer, the term of this patent is extended or adjusted under 35 U.S.C. 154(b) by 694 days.

This patent is subject to a terminal disclaimer.

(21) Appl. No.: 16/783,148

(22) Filed: Feb. 5, 2020

(65) Prior Publication Data

US 2020/0181596 A1 Jun. 11, 2020

Related U.S. Application Data

(63) Continuation-in-part of application No. 16/726,495, filed on Dec. 24, 2019, which is a continuation-in-part of application No. 16/488,103, filed as application No. PCT/US2018/022873 on Mar. 16, 2018.

(60) Provisional application No. 62/472,790, filed on Mar. 17, 2017, provisional application No. 62/531,522, filed on Jul. 12, 2017.

(51) Int. Cl.
| | | |
|---|---|---|
| *C12N 9/64* | (2006.01) | |
| *A61K 9/00* | (2006.01) | |
| *A61K 48/00* | (2006.01) | |
| *A61N 1/05* | (2006.01) | |
| *A61N 1/36* | (2006.01) | |
| *C12N 5/074* | (2010.01) | |
| *C12N 15/86* | (2006.01) | |

(52) U.S. Cl.
CPC .......... *C12N 9/6421* (2013.01); *A61K 9/0019* (2013.01); *A61K 9/0046* (2013.01); *A61K 48/0058* (2013.01); *A61N 1/0541* (2013.01); *A61N 1/36038* (2017.08); *C12N 5/0696* (2013.01); *C12N 15/86* (2013.01)

(58) Field of Classification Search
CPC .... C12N 9/6421; C12N 5/0696; C12N 15/86; C12N 2750/14143; A61K 9/0019; A61K 9/0046; A61K 48/0058; A61K 48/005; A61K 48/0075; A61N 1/0541; A61N 1/36038; A01K 2267/0306
See application file for complete search history.

(56) References Cited

U.S. PATENT DOCUMENTS

| | | |
|---|---|---|
| 7,071,004 B1 | 7/2006 | Meyers et al. |
| 10,258,697 B2 | 4/2019 | Chen et al. |
| 2002/0064856 A1* | 5/2002 | Plowman ................ A61P 11/06 435/5 |
| 2007/0009433 A1 | 1/2007 | Meyers et al. |
| 2007/0093878 A1 | 4/2007 | Edge et al. |
| 2013/0095071 A1 | 4/2013 | Bance et al. |
| 2015/0050354 A1 | 2/2015 | Bouchon et al. |
| 2015/0291966 A1 | 10/2015 | Zhang et al. |
| 2015/0329875 A1* | 11/2015 | Gregory ................ C07K 14/00 435/325 |
| 2016/0237455 A1 | 8/2016 | Glucksmann et al. |

FOREIGN PATENT DOCUMENTS

| | | |
|---|---|---|
| WO | 2004099779 A1 | 11/2004 |
| WO | 2007021423 A2 | 2/2007 |
| WO | 2011075838 A1 | 6/2011 |
| WO | 2015048577 A2 | 4/2015 |
| WO | 2015054653 A2 | 4/2015 |
| WO | 2016069910 A1 | 5/2016 |
| WO | 2017100791 A1 | 6/2017 |
| WO | 2018170402 A1 | 9/2018 |

OTHER PUBLICATIONS

Duan et al. "Treatment of peripheral sensorineural hearing loss: gene therapy." Gene therapy 11.1 (2004): S51-S56 (Year: 2004).*
Database GenBank[online], Accession No. AK057232 https://www.ncbi.nlm.nih.gov/nuccore/165 52841?sat=3&satkey=7854353 Jan. 9, 2008 uploaded, Definition: Homo sapiens cDNA FLJ32670 fis, clone TESTI1000127, weakly similar to Polycystin Precursor.
Database GenBank[online], Accession No. BC074847 https://www.ncbi.nlm.nih.gov/nuccore/50959925?sat=4&satkey=122051 709 Jul. 15, 2006 uploaded, Definition: Homo sapiens transmnernbrane protease, serine 3. mRNA (cDNA clone M GC: 1 04100 I MAGE: 30915553), complete eds.
Grillet, N. et al. "Mutations in LOXHD1, an evolutionarily conserved stereociliary protein, disrupt hair cell function in mice and cause progressive hearing loss in Humans", 2009, American Journal of Human Genetics, 85(3), pp. 328-337.

(Continued)

*Primary Examiner* — Fereydoun G Sajjadi
*Assistant Examiner* — Alexander W Nicol
(74) *Attorney, Agent, or Firm* — Blank Rome LLP

(57) ABSTRACT

The present disclosure describes gene therapy systems, and related methods, useful for treating and/or preventing deafness caused by genetic mutation of the TMPRSS3 gene or the LOXHD1 gene. The compositions and methods disclosed herein use adeno-associated viral (AAV) vector gene delivery of TRMPSS3 or LOXHD1 into the inner ear to restore activity of the TMPRSS3 gene or the LOXHD1 gene, respectively, promote hair cell survival and restore hearing in patients suffering from hearing loss. As disclosed herein, the systems and methods may utilize a combination of gene therapy (e.g., molecular therapeutics) for hearing loss caused by a genetic mutation together with implantation of a cochlear implant.

8 Claims, 11 Drawing Sheets

Specification includes a Sequence Listing.

(56) References Cited

OTHER PUBLICATIONS

Muller, U. et al. "New treatment options for hearing loss", 2015, Nature Reviews Drug Discovery, 14(5), pp. 346-365.
Ohlemiller, K. et al. "Application of Mouse Models to Research in Hearing and Balance", Journal of the Association for Research in Otolaryngology, 2016, 17(6), XP036101750.
European Supplemental Search Report EP Appln. No. 18768248.9, Corresponding to PCT/US2018/022873.
Smith, Richard JH, et al., Deafness and Hereditary Hearing Loss Overview, GeneReviews, University of Washington, eattle, Initial posting Feb. 31, 1999, Last update Jan. 9, 2014, [online], [retrieved on Mar. 7, 2017]. Retrieved from <https://www.ncbi.nlm.nih_gov/books/NBK1434?report=printable>.
Basics of OAEs, Distortion Product Otoacoustic Emissions, Otacoustic Emissions Portal [online], [retrieved on Mar. 7, 2017]. Retrieved from <http://www.oae.it/old/definitions/DPOAE.html>.
Hochmair, I. Cochlear Implants: Facts, Med-El, Sep. 2013, [retrieved on Mar. 7, 2017]. Retrieved from <http://www.medel.com/cochlear-implants-facts/>.
Centers for Disease Control and Prevention, Genetics of Hearing Loss, last update Feb. 18, 2015 [online], [retrieved Mar. 7, 2017]. Retrieved from <https://cdc.gov/ncbddd/hearingloss/genetics.html>.
Leary Swan, Erin E. et al., Inner Ear Drug Delivery for Auditory Applications, NIH Public Access Author Manuscript, 2008, pp. 1-34.
Effectual Services, Patentability Search Report, Gene Therapy for Hearing Loss, Jul. 21, 2016.
Who, Prevention of Blindness and Deafness [online], [retrieved Mar. 7, 2017]. Retrieved from <http://www.who.int/pbd/deafness/estimate/en/>.
Effectual Services, Patentability Search Report, Treatment of Congenital Hearing Loss, Jan. 11, 2017.
Shu, Y. et al., Identification of Adeno-associated viral vectors (AAV) that target neonatal and adult mammalian inner ear cell subtypes, Human Gene Therapy, Jun. 2016.
Zuris, John A. et al., Efficient Delivery of Genome-Editing Proteins In Vitro and In Vivo, HHS Public Access Author Manuscript, 2015, pp. 1-26.
Zou, B. et al., The application of genome editing in studying hearing loss, HHS Public Access Author Manuscript, 2015, pp. 1-18.
Pandey, S. & Pandey M., Advances in Genetic Diagnosis and Treatment of Hearing Loss—A Thirst for Revolution, Intech, 2015, pp. 53-89.
Vona, B. et al., DFNB16 is a frequent cause of congenital hearing impairment: implementation of STRC mutation analysis in routine diagnostics, Clinical Genetics, Short Report, 2015, pp. 49-55.
Scott, Hamish S., et al., "Insertion of B-satellite repeats identifies a transmembrane protease causing both congenital and childhood onset autosomal recessive deafness," Nature Genetics, vol. 27, No. 1, pp. 59-63, Jan. 31, 2001.
International Search Report, dated Jul. 6, 2018, for PCT/US2018/022873.
Novartis Pharmaceuticals, "Safety, Tolerability and Efficacy for CGF166 in Patients with Unilateral or Bilateral Severe-to-profound Hearing Loss," https://clinicaltrials.gov/ct2/show/record/NCT02132130, accessed Dec. 24, 2019, 9 pages.
Lzzaro, Marc A. et al., "Endovascular embolization of head and neck tumors," Frontiers in Neurology, vol. 2, Art. 64, pp. 1-9, Oct. 17, 2011.
Landegger, Lukas D, et al., "A synthetic AAV vector enables safe and efficient gene transfer to the mammalian inner ear", Nature Biotechnology, Aug. 6, 2017, vol. 35, No. 3, pp. 280-284. entire document.
Chung et al., J. Mol. Med., 2014, 92:651-663.
Sohn, Jaerin, et al., A Single Vector Platform for High-Level Gene Transduction of Central Neurons: Adeno-Associated Virus Vector Equipped with the Tet-Off System, Plos One, DOI:10.1371/journal.pone.0169611, Jan. 6, 2017, 22 pages.
Staecker, et al., "Development of gene therapy for inner ear disease: Using bilateral vestibular hypofunction as a vehicle for translational research", Hearing research 276. 1-2 (2011): 44-51 (Year: 2011).

\* cited by examiner

FIGURE 1

| | | | | | |
|---|---|---|---|---|---|
| 1 | cggatgtcag | aggtcctgaa | atagtcacca | tgggggaaaa | tgatccgcct | gctgttgaag |
| 61 | cccccttctc | attccgatcg | cttttttggcc | ttgatgattt | gaaaataagt | cctgttgcac |
| 121 | cagatgcaga | tgctgttgct | gcacagatcc | tgtcactgct | gccattgaag | ttttttccaa |
| 181 | tcatcgtcat | tgggatcatt | gcattgatat | tagcactggc | cattggtctg | ggcatccact |
| 241 | tcgactgctc | agggaagtac | agatgtcgct | catcctttaa | gtgtatcgag | ctgatagctc |
| 301 | gatgtgacgg | agtctcggat | tgcaaagacg | gggaggacga | gtaccgctgt | gtccgggtgg |
| 361 | gtggtcagaa | tgccgtgctc | caggtgttca | cagctgcttc | gtggaagacc | atgtgctccg |
| 421 | atgactggaa | gggtcactac | gcaaatgttg | cctgtgccca | actgggtttc | ccaagctatg |
| 481 | taagttcaga | taacctcaga | gtgagctcgc | tggaggggca | gttccgggag | gagtttgtgt |
| 541 | ccatcgatca | cctcttgcca | gatgacaagg | tgactgcatt | acaccactca | gtatatgtga |
| 601 | gggagggatg | tgcctctggc | cacgtggtta | ccttgcagtg | cacagcctgt | ggtcatagaa |
| 661 | ggggctacag | ctcacgcatc | gtgggtggaa | acatgtcctt | gctctcgcag | tggccctggc |
| 721 | aggccagcct | tcagttccag | ggctaccacc | tgtgcggggg | ctctgtcatc | acgcccctgt |
| 781 | ggatcatcac | tgctgcacac | tgtgtttatg | acttgtacct | ccccaagtca | tggaccatcc |
| 841 | aggtgggtct | agtttccctg | ttggacaatc | cagccccatc | ccacttggtg | gagaagattg |
| 901 | tctaccacag | caagtacaag | ccaaagaggc | tgggcaatga | catcgccctt | atgaagctgg |
| 961 | ccgggccact | cacgttcaat | gaaatgatcc | agcctgtgtg | cctgcccaac | tctgaagaga |
| 1021 | acttccccga | tggaaaagtg | tgctggacgt | caggatgggg | ggccacagag | gatggagcag |
| 1081 | gtgacgcctc | ccctgtcctg | aaccacgcgg | ccgtcccttt | gatttccaac | aagatctgca |
| 1141 | accacaggga | cgtgtacggt | ggcatcatct | cccctccat | gctctgcgcg | ggctacctga |
| 1201 | cgggtggcgt | ggacagctgc | caggggaca | gcgggggggcc | cctggtgtgt | caagagagga |
| 1261 | ggctgtggaa | gttagtggga | gcgaccagct | ttggcatcgg | ctgcgcagag | gtgaacaagc |
| 1321 | ctggggtgta | caccccgtgtc | acctccttcc | tggactggat | ccacgagcag | atggagagag |
| 1381 | acctaaaaac | ctgaaaagga | agggacaag | tagccacct | (SEQ ID NO:1) | |

FIGURE 2

MGENDPPAVEAPFSFRSLFGLDDLKISPVAPDADAVAAQILSLLPLKFFPIIVIGIIALILALAIGLGIHFD
CSGKYRCRSSFKCIELIARCDGVSDCKDGEDEYRCVRVGGQNAVLQVFTAASWKTMCSDDWKGHYANVACAQ
LGFPSYVSSDNLRVSSLEGQFREEFVSIDHLLPDDKVTALHHSVYVREGCASGHVVTLQCTACGHRRGYSSR
IVGGNMSLLSQWPWQASLQFQGYHLCGGSVITPLWIITAAHCVYDLYLPKSWTIQVGLVSLLDNPAPSHLVE
KIVYHSKYKPKRLGNDIALMKLAGPLTFNEMIQPVCLPNSEENFPDGKVCWTSGWGATEDGAGDASPVLNHA
AVPLISNKICNHRDVYGGIISPSMLCAGYLTGGVDSCQGDSGGPLVCQERRLWKLVGATSFGIGCAEVNKPG
VYTRVTSFLDWIHEQMERDLKT   (SEQ ID NO:2)

FIGURE 3

```
   1    gtagaaccga ggtgggggct tggtgaaggc acaccaggaa gagcaggctg cgcctcaccc
  61    tccagtggag acagagggca gacattctct ttggagcaca cctcaggcta aatggcaaaa
 121    ccccaatctc aagtgaactt catggaacta ggggattgtc tcacttctcc agtggattga
 181    ggcagtgctc cctctgttct ctatgaaatg acggtgtgga caggggatgt ggttggcggg
 241    ggcactgact ccaacatctt catgaccctc tacggcatca acggagcac agaggagatg
 301    cagctggaca aaagaaagc caggtttgag cgggagcaga acgacacctt catcatggag
 361    atcctagaca ttgctccatt caccaagatg cggatccgga ttgatggcct gggcagtcgg
 421    ccggagtggt tcctggagag gatcctactg aagaacatga acactggaga cctgaccatg
 481    ttctactatg gagactggct gtcccagcgg aagggcaaga agaccctggt gtgtgaaatg
 541    tgtgccgtta tcgatgagga agaaatgatg gagtggacct cctacaccgt cgcagttaag
 601    accagcgaca tcctgggagc aggcactgat gccaacgtgt tcatcatcat cttcggggag
 661    aacggggata gtgggacact ggccctgaag cagtcggcaa actggaacaa gtttgagcgg
 721    aacaacacgg acacattcaa cttccctgac atgctgagct tgggccacct ctgcaagctg
 781    aggtctggc acgacaacaa agggatattt cctggctggc atctgagcta tgtcgatgtg
 841    aaggacaact cccgcgacga gaccttccac ttccagtgtg actgctggct ctccaagagt
 901    gagggtgacg ggcagacggt ccgcgacttt gctgtgcca acaacaagat ctgtgatgag
 961    ctggaagaga ccacctacga gatcgtcata gaaacgggca acggaggcga accagggag
1021    aacgtctggc tcatcctgga gggcaggaag aaccgatcca agagtttct catggaaaat
1081    tcttctaggc agcgggcctt taggaagggg accacagaca cgtttgagtt tgacagcatc
1141    tacttggggg acattgcctc cctctgtgtg ggccaccttg ccagggaaga ccggtttatc
1201    cccaagagag aacttgcctg gcatgtcaag accatcacca tcaccgagat ggagtacggc
1261    aatgtgtacc tctttaactg tgactgcctc atcccctca agaggaagag gaagtacttc
1321    aaggtattcg aggttaccaa gacgacagag agctttgcca gcaaggtcca gagcctggtg
1381    cccgtcaagt acgaagtcat cgtgacaaca ggctatgagc caggggcagg cactgatgcc
1441    aacgtcttcg tgaccatctt tgggccaac ggagacacag gcaagcggga gctgaagcag
1501    aaaatgcgca acctcttcga gcgggcagc acagaccgct tcttcctgga gacgctggag
1561    ctgggtgagc tgcgcaagta gtgaccaggc tgggacttgc tgcagagtgt ggatgagaaa
1621    ttgagtcttc acccagggga tagaagtgga gaagcagagg ccatcaagat ggtgtatttt
1681    aagcaaaaac taattaacac ttttccccaa aaaagctagg ctaattaaat tattaccaac
1741    catatcctat aaagaactca tcttagcatc tgcttgctaa gaagtgtata cttttcccca
1801    gtttcaataa acccagtggc aagtgg    (SEQ ID NO:3)
```

FIGURE 4

```
MNNEITYYFPCQRWLAVEEDDGQLSRELLPVDESYVLPQSEEGRGGGDNNFLDNLALEQK
DKSTTFSVTIKTGVKKNAGTDANVFITLFGTQDDTGMTLLKSSKTNSDKFERDSIEIFTV
ETLDLGDLWKVRLGHDNTGKAPGWFVDWVEVDAPSLGKCMTFPCGRWLAKNEDDGSIIRD
LFHAELQTRLYTPFVPYEITLYTSDVFAAGTDANIFIIYGCDAVCTQQKYLCTNKREQK
QFFERKSASRFIVELEDVGEIIEKIRIGHNNTGMNPGWHCSHVDIRRLLPDKDGAETLTF
PCDRWLATSEDDKKTIRELVPYDIFTEKYMKDGSLRQVYKEVEEPLDIVLYSVQIFTGNI
PGAGTDAKVYITIYGDLGDTGERYLGKSENRTNKFERGTADTFIIEAADLGVIYKIKLRH
DNSKWCADWYVEKVEIWNDTNEDEFLFLCGRWLSLKKEDGRLERLFYEKEYTGDRSSNCS
SPADFWEIALSSKMADVDISTVTGPMADYVQEGPIIPYYVSVTTGKHKDAATDSRAFIFL
IGEDDERSKRIWLDYPRGKRGFSRGSVEEFYVAGLDVGIIKKIELGHDGASPESCWLVEE
LCLAVPTQGTKYMLNCNCWLAKDRGDGITSRVFDLLDAMVVNIGVKVLYEMTVWTGDVVG
GGTDSNIFMTLYGINGSTEEMQLDKKKARFEREQNDTFIMEILDIAPFTKMRIRIDGLGS
RPEWFLERILLKNMNTGDLTMFYYGDWLSQRKGKKTLVCEMCAVIDEEEMMEWTSYTVAV
KTSDILGAGTDANVFIIIFGENGDSGTLALKQSANWNKFERNNTDTFNFPDMLSLGHLCK
LRVWHDNKGIFPGWHLSYVDVKDNSRDETFHFQCDCWLSKSEGDGQTVRDFACANNKICD
ELEETTYEIVIETGNGGETRENVWLILEGRKNRSKEFLMENSSRQRAFRKGTTDTFEFDS
IYLGDIASLCVGHLAREDRFIPKRELAWHVKTITITEMEYGNVYFFNCDCLIPLKRKRKY
FKVFEVTKTTESFASKVQSLVPVKYEVIVTTGYEPGAGTDANVFVTIFGANGDTGKRELK
QKMRNLFERGSTDRFFLETLELVVTRLGLAAECG        (SEQ ID NO:4)
```

GENE THERAPY SYSTEMS AND RELATED METHODS FOR TREATMENT OF HEARING LOSS

CROSS-REFERENCE TO RELATED APPLICATIONS

The present application is a continuation-in-part application of U.S. application Ser. No. 16/726,495 filed on Dec. 24, 2019, which is a continuation-in-part of U.S. application Ser. No. 16/488,103 filed on Aug. 22, 2019, which is a national phase entry of PCT Application No. PCT/US2018/022873 filed on Mar. 16, 2018, which claims priority to U.S. Provisional Application No. 62/531,522 filed on Jul. 12, 2017, and U.S. Provisional Application No. 62/472,790 filed on Mar. 17, 2017, the contents of each of which are incorporated by reference herein in their entirety.

TECHNICAL FIELD

Various embodiments of the present disclosure relate generally to gene therapy systems and methods useful in the treatment and/or prevention of hearing loss. Exemplary embodiments described herein are directed to systems and related methods for preventing the further decline in a patient's hearing loss. More specifically, embodiments taught in this present disclosure relate to gene therapy systems, and related methods, useful for treating and/or preventing deafness caused by genetic mutation of the TMPRSS3 gene or the LOXHD1 gene. These systems and methods may utilize a combination of gene therapy (e.g., molecular therapeutics) for hearing loss caused by a genetic mutation together with implantation of a cochlear implant.

Hearing loss is the most common sensory deficit in humans. According to 2018 estimates on the magnitude of disabling hearing loss released by the World Health Organization (WHO), there are 466 million persons worldwide living with disabling hearing loss (432 million adults and 34 million children). The number of people with disabling hearing loss will grow to 630 million by 2030 and to over 900 million by 2050 (1 in 10 people). Over 90% of persons with disabling hearing loss (420 million) reside in the low-income regions of the world (WHO global estimates on prevalence of hearing loss, Prevention of Deafness WHO 2018).

There are currently no approved therapeutic agents for preventing or treating hearing loss or deafness. The current treatment option for those with disabling hearing loss is a cochlear implant. Cochlear implantation is a common procedure with a large associated healthcare cost, over $1,000,000 lifetime cost per patient (Mohr P E, et al.

(2000). The societal costs of severe to profound hearing loss in the United States; IntJ Technol Assess Health Care; 16(4): 1120-35).

The current demand for cochlear implants exceeds supply. The production rate of cochlear implant units manufactured is 50,000 units each year. Based on current birth rates and the incidence and prevalence of disabling hearing loss in newborns, 134,000 cochlear implants are needed annually to provide 1 cochlear implant for each afflicted child. This number increases if patients needing bilateral (2) cochlear implants are included.

The lifetime cost of a cochlear implant is prohibitive for most people and particularly for those living outside the developed nations where the majority of persons with disabling hearing loss reside. Therapeutic options are needed to provide cost effective alternatives to cochlear implants, especially for those persons living outside developed nations.

More than 50% of prelingual deafness is genetic i.e. hereditary (Centers for Disease Control and Prevention—Genetics of Hearing Loss). Hereditary hearing loss and deafness may be conductive, sensorineural, or a combination of both; syndromic (associated with malformations of the external ear or other organs or with medical problems involving other organ systems) or nonsyndromic (no associated visible abnormalities of the external ear or any related medical problems); and prelingual (before language develops) or postlingual (after language develops) (Richard J H Smith, MD, A Eliot Shearer, Michael S Hildebrand, PhD, and Guy Van Camp, PhD, Deafness and Hereditary Hearing Loss Overview, GeneReviews Initial Posting: Feb. 14, 1999; Last Revision: Jan. 9, 2014. More than 70% of hereditary hearing loss is nonsyndromic. The different gene loci for nonsyndromic deafness are designated DFN (for DeaFNess). Loci are named based on mode of inheritance: DFNA (Autosomal dominant), DF B (Autosomal recessive) and DFNX (X-linked). The number following the above designations reflects the order of gene mapping and/or discovery. In the general population, the prevalence of hearing loss increases with age. This change reflects the impact of genetics and environment and the interactions between environmental triggers and an individual's genetic predisposition.

Sensorineural hearing loss (SNHL) is the most common neurodegenerative disease in humans and there are currently no approved pharmacologic interventions. SNHL can be caused by genetic disorders as well as acquired through injuries such as sound trauma and ototoxicity. Genetic diagnostics have demonstrated that there are at least 100 genes causing nonsyndromic SNHL. Recent advances in genetics and gene therapy techniques have shown that rescue of a number of recessive types of deafness is possible through gene therapy (Akil et al., 2012; Askew et al., 2015). Long term gene delivery to the inner ear has been achieved using adeno associated viral vectors (AAV) (Shu, Tao, Wang, et al., 2016). The first human clinical trial to address deafness and hearing loss using a gene therapy was (CGF166) initiated on June of 2014 and completed in December of 2019. The Principal Investigator for CGF166 was Dr. Hinrich Staecker and the trial was sponsored by Novaris. (https://clinicaltrials.gov/ct2/show/NCT02132130). An ideal disease target for translational research in this domain is a recessive genetic hearing loss that affects a defined group of cells within the inner ear and occurs postnatally after the development of speech. Prevalence of the mutation is an additional consideration.

As described herein, by carefully evaluating both the incidence of common recessive causes of hearing loss and taking into account the size of the gene, it is possible to develop a gene therapy program that has an accessible and fairly common patient population. For example, although less common than other mutations, TMPRSS3 is a fairly common cause of hearing loss that is severe enough to warrant cochlear implantation. Additionally, patients with mutations in TMPRSS3 may not respond to cochlear implantation as well as patients with other mutations (Shearer et al., 2017). This presents the opportunity of targeting TMPRSS3, or other genes such as LOXHD1, as a stand-alone therapeutic or in combination with other therapeutic agents and/or cochlear implantation to improve implant outcomes for this disorder. Table 1 (adapted from (Miyagawa, Nishio, & Usami, 2016)) demonstrates that mutations in TMPRSS3 may be the most common cause of postlingual recessive hearing loss that has a fairly limited distribution within the cochlea and, due to the size of the gene, may be built into existing AAV vectors.

TABLE 1

Incidence of different mutations in 176 adult cochlear implant patients.

| MUTATION | ONSET | | | | 173 | | |
| --- | --- | --- | --- | --- | --- | --- | --- |
| | PRE | POST | TOTAL | % OF TOTAL | GENE S2 | HAIR CELL | DOM/REC |
| GIB2 | 26 | 3 | 29 | 17% | 2347 | NO | BOTH |
| CDH23 | 6 | 7 | 13 | 8% | 4843 | YES | REC |
| SLC26A4 | 8 | 0 | 8 | 5% | 4930 | NO | REC |
| MYO7A | 3 | 4 | 7 | 4% | 7465 | YES | BOTH |
| OTOF | 4 | 0 | 4 | 2% | 6973 | YES | REC |
| MYO15A | 2 | 2 | 4 | 2% | 11876 | YES | REC |
| WARDNB SYN | 3 | 0 | 3 | 2% | 1504 | NO | DOM |
| TMPRSR83 | 0 | 3 | 3 | 2% | 2460 | YES | REC |
| ACTG1 | 0 | 2 | 2 | 2% | 2123 | YES | DOM |
| USHER (1 = CDH23, 1 = PCDH15) | 2 | 0 | 2 | 1% | 4848, 7042 | ? | REC |
| Mt555A > G | 0 | 2 | 2 | 1% | NA | ? | ? |
| CYRM | 0 | 1 | 1 | 1% | 1559 | NO | DOM |
| DFNA5 | 0 | 1 | 1 | 1% | 2276 | YES | DOM |
| COCH | 0 | 1 | 1 | 1% | 2882 | NO | DOM |
| WHRN | 0 | 1 | 1 | 1% | 2915 | YES | REC |
| LOXHD1 | 1 | 0 | 1 | 1% | 3978 | YES | REC |
| Mt3245A>G | 0 | 1 | 1 | 1% | NA | ? | ? |

The human transmembrane protease, serine 3 (TMPRSS3; also referred to as DFNB10, DFNB8, ECHOS1, TADG12; Acc: HGNC:11877) was identified by its association with both congenital (present at birth) and childhood onset autosomal recessive deafness. Mutations in the TMPRSS3 gene are associated with Autosomal Recessive Nonsyndromic Hearing Impairment type DFNB8 and 10. TMPRSS3 is a 1646 base pair gene that codes for a serine protease and is associated with DFNA 8/10 and may make up to 1-5% of patients with hearing loss undergoing cochlear implantation (Weegerink et al., 2011). Loss of function of this gene appears to result in a broad spectrum of hearing phenotypes depending on the site of the mutation. Both congenital and adult onset progressive hearing loss have been associated with the loss of this gene.

The onset of DFNB8 hearing loss is postlingual (age 10-12 years), while the onset of DFNB10 hearing loss is prelingual (congenital). This phenotypic difference reflects a genotypic difference. The DFNB8 causing variant is a splice site variant, suggesting that inefficient splicing is associated with a reduced amount of normal protein that is sufficient to prevent prelingual deafness but not sufficient to prevent eventual hearing loss. (See, Richard J H Smith, M D, et al. (2014). Genes Known to Cause Autosomal Recessive Nonsyndromic Hearing Impairment: Deafness and Hereditary Hearing Loss Overview; GeneReviews).

TMPRSS3 mutations on chromosome 21 known to cause hearing loss are described in Table 2.

TABLE 2

TMPRSS3 MUTATIONS (CHROMOSOME 21)

| # | MUTATION NAME | REFERENCE |
| --- | --- | --- |
| 1 | TMPRSS3, IVS4AS, G-A, −6 | Scott H S, et al. (2001) Insertion of beta-satellite repeats identifies a transmembrane protease causing both congenital and childhood onset autosomal recessive deafness. *Nat Genet.* 27(1): 59-63. |
| 2 | TMPRSS3, 8-BP DEL, SATELLITE REPEAT INS | Scott H S, et al. (2001) Insertion of beta-satellite repeats identifies a transmembrane protease causing both congenital and childhood onset autosomal recessive deafness. *Nat Genet.* 27(1): 59-63. |
| 3 | TMPRSS3, 1-BP DEL, 207C | Wattenhofer M, et al. (2002) Mutations in the TMPRSS3 gene are a rare cause of childhood nonsyndromic deafness in Caucasian patients. *J Mol Med (Berl).* 80(2): 124-31. |
| 4 | c.753G>C (p.Trp251Cys) | Masmoudi S, et al. (2001) Novel missense mutations of TMPRSS3 in two consanguineous Tunisian families with non-syndromic autosomal recessive deafness. *Hum Mutat.* 18(2): 101-8. |
| 5 | c.308A>G (p.Asp103Gly) | Wattenhofer M, et al. (2002) Mutations in the TMPRSS3 gene are a rare cause of childhood nonsyndromic deafness in Caucasian patients. *J Mol Med (Berl).* 80(2): 124-31. |
| 6 | c.1211C>T (p.Pro404Leu) | Wattenhofer M, et al. (2005) A novel TMPRSS3 missense mutation in a DFNB8/10 family prevents proteolytic activation of the protein. *Hum Genet.* 117(6): 528-35. |
| 7 | c.647G>T (p.Arg216Leu) | Wattenhofer M, et al. (2005) A novel TMPRSS3 missense mutation in a DFNB8/10 family prevents proteolytic activation of the protein. *Hum Genet.* 117(6): 528-35. |

TABLE 2-continued

TMPRSS3 MUTATIONS (CHROMOSOME 21)

| # | MUTATION NAME | REFERENCE |
|---|---|---|
| 8 | c.579dupA (p.Cys194Metfs) | Duzkale H, et al. (2013) A systematic approach to assessing the clinical significance of genetic variants. Clin Genet. 84(5): 453-63. |
| 9 | c.1192C>T (p.Gln398Ter) | Wattenhofer M, et al. (2005) A novel TMPRSS3 missense mutation in a DFNB8/10 family prevents proteolytic activation of the protein. Hum Genet. 117(6): 528-35. |
| 10 | c.323-6G>A | Scott H S, et al. (2001) Insertion of beta-satellite repeats identifies a transmembrane protease causing both congenital and childhood onset autosomal recessive deafness. Nat Genet. 27(1): 59-63. |
| 11 | c.916G>A (p.Ala306Thr) | Chung J, et al. (2014) A novel mutation of TMPRSS3 related to milder auditory phenotype in Korean postlingual deafness: a possible future implication for a personalized auditory rehabilitation. J Mol Med (Berl). 92(6): 651-63. |
| 12 | c.208delC (p.His70Thrfs) | Battelino S, et al. (2015) TMPRSS3 mutations in autosomal recessive nonsyndromic hearing loss. Eur Arch Otorhinolaryngol. 273(5): 1151-4. |
| 13 | c.1276G>A (p.Ala426Thr) | Weegerink N J, et al. (2011) Genotype-phenotype correlation in DFNB8/10 families with TMPRSS3 mutations. J Assoc Res Otolaryngol. 12(6): 753-66. |
| 14 | c.413C>A (p.Ala138Glu) | Eppsteiner R W, et al. (2012) Prediction of cochlear implant performance by genetic mutation: the spiral ganglion hypothesis. Hear Res. 292(1-2): 51-8. |
| 15 | c.325C>T (p.Arg109Trp) | Lee Y J, Park D, Kim S Y, Park W J (2003) Pathogenic mutations but not polymorphisms in congenital and childhood onset autosomal recessive deafness disrupt the proteolytic activity of TMPRSS3. J Med Genet. 40(8): 629-31. |
| 16 | c.346G>A (p.V116M) | Ganapathy A, et al. (2014) Non-syndromic hearing impairment in India: high allelic heterogeneity among mutations in TMPRSS3, TMC1, USHIC, CDH23 and TMIE. PLoS One. 9(1): e84773. |
| 17 | c.727G>A (p.G243R) | Ganapathy A, et al. (2014) Non-syndromic hearing impairment in India: high allelic heterogeneity among mutations in TMPRSS3, TMC1, USHIC, CDH23 and TMIE. PLoS One. 9(1): e84773. |
| 18 | c.1156T>C (p.C386R) | Ganapathy A, et al. (2014) Non-syndromic hearing impairment in India: high allelic heterogeneity among mutations in TMPRSS3, TMC1, USHIC, CDH23 and TMIE. PLoS One. 9(1): e84773. |

The lipoxygenase homology domains 1 gene (LOXHD1; also referred to as LH2D1, DFNB77, FLJ32670; OMIM: 613072; Acc:HGNC:26521) encodes a highly conserved protein consisting entirely of PLAT (polycystin/lipoxygenase/alpha-toxin) domains, thought to be involved in targeting proteins to the plasma membrane. Studies in mice show that this gene is expressed in the mechanosensory hair cells in the inner ear, and mutations in this gene lead to auditory defects, indicating that this gene is essential for normal hair cell function. Screening of human families segregating deafness identified a mutation in this gene which causes DFNB77, a progressive form of autosomal-recessive nonsyndromic hearing loss (ARNSHL). Alternatively spliced transcript variants encoding different isoforms have been noted for this gene.

Clinical Features of LOXHD1:
  Autosomal recessive
  Hearing loss, sensorineural, bilateral (milder hearing loss at low frequencies)
  Congenital onset leading to cochlear implants between 7-10 years of age in Ashkenazi Jewish families
  Onset by 7-8 years of age progressing to moderate-to-severe loss of mid and high frequencies during adulthood in a consanguineous Iranian family Evidence that autosomal recessive nonsyndromic hearing loss-77 (DFNB77) is caused by homozygous mutation in the LOXHD1 gene (613072) on chromosome 18q21.

In situ hybridization detected Loxhd1 expression in the developing mouse inner ear at embryonic days 13.5 and 16, but not in any other tissue. At postnatal day 4, expression was detected in cochlear and vestibular hair cells, with highest concentration in the nucleus. Loxhd1 progressively localized to the cytoplasm, and in the adult, Loxhd1 was expressed in hair cells along the length of stereocilia.

Using an N-ethyl-N-nitrosourea (ENU) mutagenesis screen, Grillet et al. (2009) developed the 'samba' mouse line that becomes hearing impaired by 3 weeks of age and deaf by 8 weeks of age. Homozygous samba mice showed no other neurologic or vestibular abnormalities, and heterozygous samba mice appeared completely normal. Stereociliary development was not affected in homozygous samba mice, but hair cell function was perturbed and hair cells eventually degenerated.

Grillet et al. (2009) found that samba was a mutation in the mouse Loxhd1 gene that destabilized the beta-sandwich structure of PLAT domain 10. The mutation did not alter mRNA or protein stability or localization of Loxhd1 protein along the length of stereocilia. However, by postnatal day 21, some hair cells showed morphologic defects with fused stereocilia and membrane ruffling at the apical cell surface. Profound degenerative changes were obvious by postnatal day 90, including hair cell loss and a reduction in spiral ganglion neurons. Grillet et al. (2009) hypothesized that the degeneration of spiral ganglion neurons was likely secondary to perturbations in the function and maintenance of hair cells.

LOXHD1 mutations on chromosome 18 known to cause hearing loss are described in Table 3.

TABLE 3

LOXHD1 MUTATIONS (CHROMOSOME 18)

| # | MUTATION NAME | REFERENCE |
|---|---|---|
| 1 | c.2008C>T (p.Arg670Ter) | Grillet N, et al. (2009) Mutations in LOXHD1, an evolutionarily conserved stereociliary protein, disrupt hair cell function in mice and cause progressive hearing loss in humans. *Am J Hum Genet.* 85(3): 328-37. |
| 2 | c.3169C>T (p.Arg1057Ter) | Edvardson S, et al. (2011) A deleterious mutation in the LOXHD1 gene causes autosomal recessive hearing loss in Ashkenazi Jews. *Am J Med Genet A.* 155A(5): 1170-2. Grillet N, et al. (2009) Mutations in LOXHD1, an evolutionarily conserved stereociliary protein, disrupt hair cell function in mice and cause progressive hearing loss in humans. *Am J Hum Genet.* 85(3): 328-37. |
| 3 | c.2303delG (p.Gly768Alafs) | Edvardson S, et al. (2011) A deleterious mutation in the LOXHD1 gene causes autosomal recessive hearing loss in Ashkenazi Jews. *Am J Med Genet A.* 155A(5): 1170-2. Grillet N, et al. (2009) Mutations in LOXHD1, an evolutionarily conserved stereociliary protein, disrupt hair cell function in mice and cause progressive hearing loss in humans. *Am J Hum Genet.* 85(3): 328-37. |
| 4 | c.4099G>T (p.Glu1367Ter) | Edvardson S, et al. (2011) A deleterious mutation in the LOXHD1 gene causes autosomal recessive hearing loss in Ashkenazi Jews. *Am J Med Genet A.* 155A(5): 1170-2. Grillet N, et al. (2009) Mutations in LOXHD1, an evolutionarily conserved stereociliary protein, disrupt hair cell function in mice and cause progressive hearing loss in humans. *Am J Hum Genet.* 85(3): 328-37. |
| 5 | c.2497C>T (p.Arg833Ter) | Edvardson S, et al. (2011) A deleterious mutation in the LOXHD1 gene causes autosomal recessive hearing loss in Ashkenazi Jews. *Am J Med Genet A.* 155A(5): 1170-2. Grillet N, et al. (2009) Mutations in LOXHD1, an evolutionarily conserved stereociliary protein, disrupt hair cell function in mice and cause progressive hearing loss in humans. *Am J Hum Genet.* 85(3): 328-37. |
| 6 | c.4714C>T | Edvardson S, et al. (2011) A deleterious mutation in the LOXHD1 gene causes autosomal recessive hearing loss in Ashkenazi Jews. *Am J Med Genet A.* 155A(5): 1170-2. |

U.S. Application Publication No. 2013/0095071, incorporated by reference herein in its entirety, describes gene therapy methods for restoring age-related hearing loss using mutated tyrosine adeno-associated viral vectors to deliver the X-linked inhibitor of apoptosis protein (XIAP) to the round window membrane of the inner ear. However, the publication does not contemplate the delivery of a nucleic acid sequence encoding functional TMPRSS3 or LOXHD1 to prevent or delay the onset of or restore hearing loss or deafness caused by genetic mutation of the TMPRSS3 or LOXHD1 gene, as disclosed herein.

Additionally, an important pitfall in the current state of the art for developing clinical gene therapies for hearing disorders is a lack of animal models that mirror human hearing loss. Many of the available mouse models for genetic hearing losses with adult onset in humans present with congenital hearing loss making delivery studies complex. There are few models with onset of genetic hearing loss after development of hearing. Delivery of vectors in neonatal mice results in different transfection patterns than delivery in adult mice (Shu, Tao, Li, et al., 2016). There is a need for novel animal models that can be used to evaluate rescue of hearing using different vector systems and gene targets.

In view of the above, cochlear implantation is one common method of treatment of choice for addressing hearing loss ranging from severe to profound. A cochlear implant is a small, complex electronic device that can help to provide a sense of sound to a person who is profoundly deaf or severely hard-of-hearing. The implant consists of an external portion that sits behind the ear and a second portion that is surgically placed under the skin.

While tremendous advances in cochlear implant design and performance have occurred over the years, there are still patients who do poorly in terms of speech outcomes with implants. Recent studies have demonstrated that mutations in the two genes that cause deafness, TMPRSS3 and LoxHD1, also have poor outcomes in cochlear implant results[1]. Specifically, the TMPRSS3 mutant patient has dysfunction of their spiral ganglion[2]. During evaluation of a mouse TMPRSS3 mutant model, it was demonstrated that hair cells degenerated initially and was followed shortly after by the degeneration of spiral ganglion cells[3]. Permanent damage to the hair cells of the inner ear results in sensorineural hearing loss, leading to communication difficulties in a large percentage of the population. Hair cells are the receptor cells that transduce the acoustic stimulus. Regeneration of damaged hair cells would provide an avenue for the treatment of a condition that currently has no therapies other than prosthetic devices.

During evaluation of human patients with TMPRSS3 mutations, it was demonstrated that cochlear implant function declines with age, which suggests that the delayed degeneration of spiral ganglion cells also occurs in the human population[4]. The foregoing suggests that cochlear implants alone may not be enough to combat hearing loss.

Opportunities, therefore, exist to provide a combination of molecular therapeutics (e.g., gene therapy) for hearing loss in combination with cochlear implantation.

SUMMARY

Embodiments of the present disclosure relate to, among other things, gene therapy systems and methods useful in treating and/or preventing hearing loss. Systems and methods described herein relate to combination gene therapy with cochlear implantation to repair and/or rescue degenerating hair cells and/or degenerating spiral ganglion cells depending on the time of intervention.

Each of the embodiments disclosed herein may include one or more of the features described in connection with any of the other disclosed embodiments.

Disclosed herein is an expression vector including the nucleic acid sequence of SEQ ID NO:1 or SEQ ID NO:2, or a nucleic acid sequence having at least 90% sequence identity to the nucleic acid of SEQ ID NO:1 or SEQ ID NO:2, wherein the nucleic acid sequence is operatively linked to a promoter. Also disclosed herein is a pharmaceutical composition for use in a method for the treatment or prevention of hearing loss that includes an expression vector having the nucleic acid sequence of SEQ ID NO:1 or SEQ ID NO:2, or a nucleic acid sequence having at least 90% sequence identity to the nucleic acid of SEQ ID NO:1 or SEQ ID NO:2, wherein the nucleic acid sequence is operatively linked to a promoter. In some embodiments, the nucleic acid sequence has at least 75%, at least 80%, at least 85%, at least 90%, at least 95%, at least 96%, at least 97%, at least 98%, or at least 99% sequence identity to the nucleic acid sequence of SEQ ID NO:1 or SEQ ID NO:2. In some embodiments, the expression vector is selected from an adeno-associated viral vector, an adenoviral vector, a herpes simplex viral vector, a vaccinia viral vector, a helper dependent adenoviral vector or a lentiviral vector. In some embodiments, the vector is an adeno-associated viral vector selected from AAV2, AAV2/Anc80, AAV5, AAV6, AAV6.2, AAV7, AAV8, AAV9, AAVrh8, AAVrh10, AAVrh39, AAVrh43AAV1, AAV2, AAV3, AAV4, AAV5, AAV6, AAV7, AAV8, Anc80, or a synthetic version of an adeno associated viral vector serotype. In some embodiments, the adeno-associated viral vector is AAV2, Anc80, or a synthetic version of an adeno associated viral vector serotype. In some embodiments, the promoter is selected from any hair cell promoter that drives the expression of an operably linked nucleic acid at early development and maintains expression throughout the life, for example, TMPRSS3 promoters, human cytomegalovirus (HCMV) promoters, cytomegalovirus/chicken beta-actin (CBA) promoters, Myo7a promoters or Pou4f3 promoters.

Disclosed herein is a cell having an expression vector that includes the nucleic acid sequence of SEQ ID NO:1 or SEQ ID NO:2, or a nucleic acid sequence having at least 90% sequence identity to the nucleic acid of SEQ ID NO:1 or SEQ ID NO:2, wherein the nucleic acid sequence is operatively linked to a promoter. In some embodiments, the nucleic acid sequence has at least 75%, at least 80%, at least 85%, at least 90%, at least 95%, at least 96%, at least 97%, at least 98%, or at least 99% sequence identity to the nucleic acid sequence of SEQ ID NO:1 or SEQ ID NO:2. In some embodiments, the cell is a stem cell. In some embodiments, the stem cell is an induced pluripotent stem cell.

Disclosed herein is a method for treating or preventing hearing loss, including administering to a subject in need thereof an effective amount of an expression vector that includes the nucleic acid sequence of SEQ ID NO:1 or SEQ ID NO:2, or a nucleic acid sequence having at least 90% sequence identity to the nucleic acid of SEQ ID NO:1 or SEQ ID NO:2, wherein the nucleic acid sequence is operatively linked to a promoter. In some embodiments, the nucleic acid sequence has at least 75%, at least 80%, at least 85%, at least 90%, at least 95%, at least 96%, at least 97%, at least 98%, or at least 99% sequence identity to the nucleic acid sequence of SEQ ID NO:1 or SEQ ID NO:2. In some embodiments, the expression vector is selected from an adeno-associated viral vector, an adenoviral vector, a herpes simplex viral vector, a vaccinia viral vector, a helper dependent adenoviral vector or a lentiviral vector. In some embodiments, the vector is an adeno-associated viral vector selected from AAV2, AAV2/Anc80, AAV5, AAV6, AAV6.2, AAV7, AAV8, AAV9, AAVrh8, AAVrh10, AAVrh39, AAVrh43, AAV1, AAV2, AAV3, AAV4, AAV5, AAV6, AAV7, AAV8 or Anc80, or a synthetic version of an adeno associated viral vector serotype. In some embodiments, the adeno-associated viral vector is AAV2, Anc80, or a synthetic version of an adeno associated viral vector serotype.s In some embodiments, the promoter is selected from any hair cell promoter that drives the expression of an operably linked nucleic acid sequence at early development and maintains expression throughout the life, for example, TMPRSS3 promoters, human cytomegalovirus (HCMV) promoters, cytomegalovirus/chicken beta-actin (CBA) promoters, Myo7a promoters or Pou4f3 promoters. In some embodiments, the expression vector is administered into the inner ear of the subject, for example, by injection. In some embodiments, the delivery method is selected from cochleostomy, round window membrane, canalostomy or any combination thereof (see, Erin E. Leary Swan, et al. (2008) Inner Ear Drug Delivery for Auditory Applications. Adv Drug Deliv Rev. 60(15):1583-1599). In some embodiments, the expression vector is delivered into the scala media via the endolymphatic sac (Colletti V, et al. (2010) Evidence of gadolinium distribution from the endolymphatic sac to the endolymphatic compartments of the human inner ear. Audiol Neurootol. 15(6):353-63; Marco Mandala, M D, et al. (2010) Induced endolymphatic flow from the endolymphatic sac to the cochlea in Ménière's disease. Otolaryngology—Head and Neck Surgery. 143, 673-679; Yamasoba T, et al. (1999) Inner ear transgene expression after adenoviral vector inoculation in the endolymphatic sac. Hum Gene Ther. 10(5):769-74). In some embodiments, the subject has one or more genetic risk factors associated with hearing loss. In some embodiments, one of the genetic risk factors is a mutation in the TMPRSS3 gene. In some embodiments, the mutation in the TMPRSS3 gene is selected from any one or more TMPRSS3 mutations known to cause hearing loss (see, for example, Table 2). In some embodiments, one of the genetic risk factors is a mutation in the LOXHD1 gene. In some embodiments, the mutation in the LOXHD1 gene is selected from any one or more LOXHD1 mutations known to cause hearing loss (see, for example, Table 3). In some embodiments, the subject does not exhibit any clinical indicators of hearing loss.

In some embodiments, an expression vector described herein is administered as a combination therapy with one or more expression vectors comprising other nucleic acid sequences and/or with one or more other active pharmaceutical agents for treating hearing loss. For example, a combination therapy may include a first expression vector that has the nucleic acid sequence of SEQ ID NO:1 and a second expression vector that has the nucleic acid sequence of SEQ ID NO:2, wherein both expression vectors are administered to a subject as part of a combination therapy to treat hearing loss.

Disclosed herein is a transgenic mouse having a human TMPRSS3 gene with a mutation selected from any one or more TMPRSS3 mutation known to cause hearing loss (see, for example, Table 2). Disclosed herein is a transgenic mouse having a human LOXHD1 gene with a mutation selected from any one or more LOXHD1 mutation known to cause hearing loss (see, for example, Table 3).

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIG. 1 shows a cDNA sequence encoding wild-type human TMPRSS3 (GenBank Accession No. BC074847.2).

FIG. 2 shows the wild-type human TMPRSS3 amino acid sequence encoded by the cDNA in FIG. 1.

FIG. 3 shows a cDNA sequence encoding wild-type human LOXHD1 (GenBank Accession No. AK057232.1).

FIG. 4 shows the wild-type human LOXHD1 amino acid sequence encoded by the cDNA in FIG. 3.

DETAILED DESCRIPTION

Figure 5:
FIG. 5 shows TMPRSS3 immunohistochemistry in the adult mouse cochlea.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

The present disclosure is drawn to gene therapy systems, and related methods, useful for treating and/or preventing deafness caused by genetic mutation. Examples of two genes that can mutate to cause deafness are the TMPRSS3 gene or the LoxHD1 gene. The systems and methods described herein may utilize a combination of gene therapy (e.g., molecular therapeutics) for hearing loss caused by a genetic mutation together with implantation of a cochlear implant. It can be appreciated that while the systems and methods are in view of gene mutations caused by either the TMPRSS3 gene or the LoxHD1 gene, other gene mutations may be targeted for repair that have been found to cause deafness or hearing loss.

For purposes of the present disclosure, the following definition of "gene therapy" may be used. Gene therapy may refer to when DNA is introduced into a patient to treat a genetic disease. The new DNA usually contains a functioning gene to correct the effects of a disease-causing mutation in the existing gene. Gene transfer, either for experimental or therapeutic purposes, relies upon a vector or vector system to shuttle genetic information into target cells. The vector or vector system is considered the major determinant of efficiency, specificity, host response, pharmacology, and longevity of the gene transfer reaction. Currently, the most efficient and effective way to accomplish gene transfer is using vectors or vector systems based on viruses that have been made replication-defective (PCT Publication No. WO 2015/054653; Methods of Predicting Ancestral Virus Sequences and Uses Thereof).

As used herein, the terms "treat," "treating," and "treatment" encompass a variety of activities aimed at desirable changes in clinical outcomes. For example, the term "treat", as used herein, encompasses any activity aimed at achieving, or that does achieve, a detectable improvement in one or more clinical indicators or symptoms of hearing loss, as described herein.

LOXHD1 gene (for example, as detected in a genetic diagnostic test) but does not yet exhibit clinical indicators or symptoms of hearing loss, thus providing a window during which therapeutic intervention can be initiated. Accordingly, in some embodiments, the present invention provides methods for therapeutic intervention during the period of gradual regression of hearing. The methods of the present invention can be commenced prior to such time period. The methods of treating hearing loss provided by the invention include, but are not limited to, methods for preventing or delaying the onset of hearing loss or the progression of clinical indicators or symptoms of hearing loss.

As used herein, the term "hearing loss" is used to describe the reduced ability to hear sound, and includes deafness and the complete inability to hear sound.

The terms "effective amount" or "therapeutically effective amount," as used herein, refer to an amount of an active agent as described herein that is sufficient to achieve, or contribute towards achieving, one or more desirable clinical outcomes, such as those described in the "treatment" description above. An appropriate "effective" amount in any individual case may be determined using standard techniques known in the art, such as a dose escalation study. The term "active agent" as used herein refers to a molecule (for example, an AAV vector described herein) that is intended to be used in the compositions and methods described herein and that is intended to be biologically active, for example, for the purpose of treating hearing loss.

The term "pharmaceutical composition" as used herein refers to a composition comprising at least one active agent as described herein or a combination of two or more active agents, and one or more other components suitable for use in pharmaceutical delivery such as carriers, stabilizers, diluents, dispersing agents, suspending agents, thickening agents, excipients, and the like.

The terms "subject" or "patient" as used interchangeably herein encompass mammals, including, but not limited to, humans, non-human primates, rodents (such as rats, mice and guinea pigs), and the like. In some embodiments of the invention, the subject is a human.

As used herein, the terms "vector" or "vectors" may be used. A "vector" may refer to a virus capable of transferring the desired gene into cells, but not capable of taking over or harming cells. To date, adenovirus, adeno-associated virus, herpes simplex virus, vaccinia virus, retrovirus, helper dependent adenovirus and lentivirus have all tested for cochlear gene delivery. Of these, the one that has demonstrated the most potential is adeno associated virus (AAV): it is non-replicating, can efficiently transfer transgenes to the inner ear, and causes no ototoxicity. In particular, AAV can effectively transfect inner hair cells, a critical feature if one hopes to correct genetic defects due to hair cell-specific mutations. To date, a number of different AAV subtypes have been used with success for cochlear gene delivery, demonstrating little if any damage to the organ of Corti. A recent report studying AAV serotypes 1, 2, 5, 6 and 8 demonstrated successful gene expression in hair cells, supporting cells, the auditory nerve and spiral ligament, with hair cells being the most effectively transduced (Lawrence R. Lustig, MD and Omar Akil, PhD (2012) Cochlear Gene Therapy. Curr Opin Neurol. 25(1): 57-60). Examples of AAV vectors that can be administered to the inner ear are further described in U.S. Patent Application No. 2013/0095071, which is incorporated herein by reference in its entirety.

There are currently no approved therapeutic agents for preventing or treating hearing loss or deafness. The current treatment option for those with disabling hearing loss is a cochlear implant. As described herein, by carefully evaluating both the incidence of common recessive causes of hearing loss and taking into account the size of the gene, it is possible to develop a combination treatment therapy system that can be accessible to the common patient population.

Cochlear implants function by bypassing the function of hair cells and directly stimulate spiral ganglion cells. Hair cells are the sensory receptors of both the auditory system and the vestibular system in the ears of all vertebrates. Through mechanotransduction, hair cells detect movement in their environment. However, these cells can deteriorate in certain animals (e.g., humans) because of a mutation in one or more genes (e.g., TMPRSS3, LoxHD1, etc). The spiral (cochlear) ganglion is the group of nerve cells that serve the sense of hearing by sending a representation of sound from the cochlea to the brain. The cell bodies of the spiral ganglion neurons are found in the modiolus, the conical shaped central axis in the cochlea. Therefore, having a functional spiral ganglion is vital for having a cochlear implant function optimally. However, as previously described, these spiral ganglion cells may be susceptible to genetic mutation that result in hearing impairment or hearing loss. Hair cells, as mentioned, may also be susceptible to genetic mutation that may also result in hearing loss or impairment.

According to an aspect of the present disclosure, delivery of a native copy of the TMPRSS3 gene (or any other suitable gene), via a viral vector, may be used to treat either hair cells and/or spiral ganglion cells depending on the vector and the promoters used. Depending on the level of deterioration of the hair cells and/or spiral ganglion cells Depending on the time of intervention, TMPRSS3 has the potential to rescue degenerating hair cells and/or degenerating spiral ganglion cells. For patients undergoing cochlear implantation because of the degree of hearing loss they have experienced, TMPRSS3 gene therapy may enhance implant function by preserving spiral ganglion function and preventing further degeneration thereby allowing the implant to function optimally given the underlying cellular substrate.

TMPRSS3 is a fairly common cause of hearing loss that is severe enough to warrant cochlear implantation. Additionally, patients with mutations in TMPRSS3 may not respond to cochlear implantation as well as patients with other mutations (Shearer et al., 2017). This presents the opportunity of targeting TMPRSS3, or other genes such as LOXHD1, as a stand-alone therapeutic or in combination with other therapeutic agents and/or cochlear implantation to improve implant outcomes for this disorder. It has been documented that mutations in TMPRSS3 may be the most common cause of postlingual recessive hearing loss that has a fairly limited distribution within the cochlea and, due to the size of the gene, may be built into existing AAV vectors.

U.S. Application Publication No. 2013/0095071, incorporated by reference herein in its entirety, describes gene therapy methods for restoring age-related hearing loss using mutated tyrosine adeno-associated viral vectors to deliver the X-linked inhibitor of apoptosis protein (XIAP) to the round window membrane of the inner ear. However, the publication does not contemplate the delivery of a nucleic acid sequence encoding functional TMPRSS3 or LOXHD1 to prevent or delay the onset of or restore hearing loss or deafness caused by genetic mutation of the TMPRSS3 or LOXHD1 gene, as disclosed herein.

Figure 11:
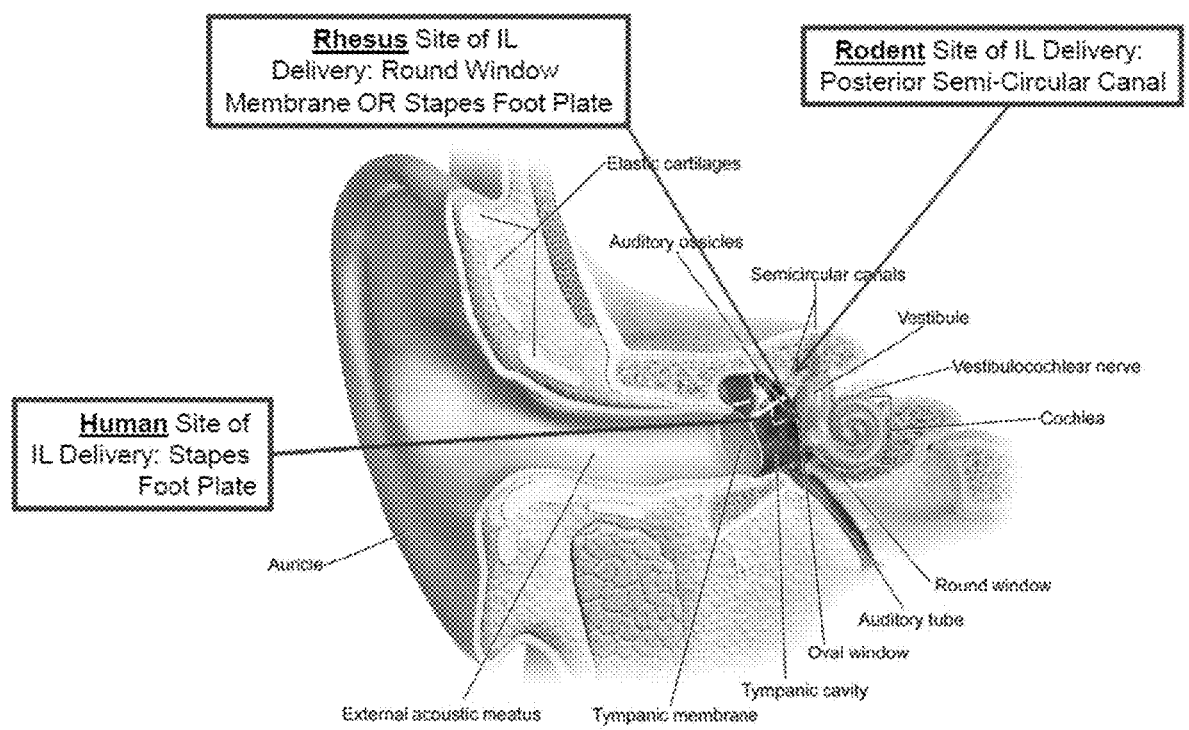
FIG. 11 illustrates the location of the Round Window Membrane (RWM) within the human ear as an exemplary drug delivery site for delivering one or more of the gene therapies taught herein.

In an exemplary embodiment, and as taught herein, the therapeutic treatment may be delivered through the round window membrane (RMW) of the inner ear using a catheter or port in the cochlear implant, as depicted in FIG. 11. In an exemplary embodiment, the round window membrane (RMW) within the human inner ear may serve as a potential drug delivery site. FIG. 11 is an annotated version of an image of the anatomy of the human ear, available at https://commons.wikimedia.org/wiki/File:
Blausen_0328_EarAnatomy.png. See Blausen.com staff (2014). "Medical gallery of Blausen Medical 2014". WikiJournal of Medicine 1 (2).

As mentioned above, there are currently no approved therapeutic treatments for preventing or treating hearing loss or deafness and there is a lack of useful preclinical animal models for testing such treatments. The present disclosure therefore describes systems and methods for viral vector gene delivery of TMPRSS3 or LOXHD1 into the inner ear to restore activity of a mutated TMPRSS3 or LOXHD1 gene, promote hair cell survival and restore hearing in patients suffering from hearing loss or deafness, and cell-based and animal-based models for testing such compositions and methods, while also combining treatment with cochlear implantation.

Hearing loss related to mutations in TMPRSS3 (DFNA8/10) can present in a variety of different phenotypes. Both congenital profound hearing loss has been described as well as adult onset progressive hearing losses (Weegerink et al., 2011). Currently, the mechanism by which Tmprss3 dysfunction is unknown. Two mouse models have been developed to date hearing loss at birth and another with onset of hearing loss slightly later time point but still before the maturation of hearing and the mouse. Fasquelle et al. generated an ethyl-nitrosourea-induced mutant mouse carrying a protein-truncating nonsense mutation in Tmprss3. This demonstrated loss of hair cells and degeneration of hearing at post-natal day 12, around the time of maturation of hearing. Additionally saccular hair cells were affected and a delayed degeneration of spiral ganglion cells were noted (Fasquelle et al., 2011). It is unclear from the mouse model whether degeneration of the spiral ganglion is related to degeneration of the organ of Corti or due to dysfunction of Tmprss3 in the spiral ganglion. A number of studies have evaluated the distribution of Tmprrss3 within the mouse inner ear and largely demonstrate presence of Tmprss3 in hair cells and spiral ganglion cells (Fan, Zhu, Li, Ji, & Wang, 2014; Fasquelle et al., 2011). Expression of mouse Tmprss3 was evaluated in 1 month old C57B15 mice using antibody anti-TMPRSS3 (1:100, ab167160, Abcam, Cambridge, MA). Labelling was seen in inner and outer hair cells, the stria vascularis and in about 50% of spiral ganglion cells (FIG. 5). This suggests that loss of TMPRSS3 function could additionally result in loss of strial function although no changes in endocochlear potential were seen in the Fasquelle mouse model (Fasquelle et al., 2011).

TMPRSS3 genotype-phenotype studies demonstrate a wide range of different forms of hearing loss ranging from profound congenital to adult onset progressive hearing losses (Chung et al., 2014; Gao et al., 2017; Weegerink et al., 2011). Studies suggest that hearing loss due to TMPRSS3 mutations may make up 2 to 5% of patients undergoing adult cochlear implantation (Jolly et al., 2012; Miyagawa, Nishio, & Usami, 2016; Sloan-Heggen et al., 2016). Many of the patients with these mutations have significant amounts of residual hearing. This would make it an attractive target for potential rescue therapy since there would be a substrate of cells that can be treated. There are some divergent studies on the success of cochlear implantation in patients with this mutation. At least some forms of hearing loss induced by loss of TMPRSS3 may not do as well with cochlear implantation than other forms of genetic deafness (Shearer et al., 2017). This is potentially related to the fact that this gene is expressed both in hair cells and in up to 50% of spiral ganglion cells (see FIG. 5). These discrepancies need to be considered when choosing a vector system for delivery. Vectors will be tested with strong hair cell tropism and combined hair cell and spiral ganglion tropism. Differences in vector tropism have also been seen when comparing neonatal and adult inner ear delivery (Shu, Tao, Li, et al., 2016; Shu, Tao, Wang, et al., 2016a). Since the target clinical population are humans with a mature auditory system, disclosed herein is a mouse model that has onset of hearing loss after maturation of hearing in which can be used as a model for both disease progression (see Example 1) and model delivery of rescue therapy to the adult cochlea (see Example 2).

Therefore, an object of the present disclosure is to provide opportunities for using a combination the gene therapy techniques described above together with with cochlear implantation.

Exemplary Embodiments

According an exemplary embodiment, the gene therapy techniques taught herein may be delivered in combination with cochlear implantation. In an exemplary embodiment, and with reference to FIG. 1 of the Appendix, a cochlear implant may comprise: 1) a microphone, which may receive sound from the environment; 2) a speech processor, which may select and arrange sounds picked up by the microphone; 3) a transmitter and receiver/stimulator, which may be configured to receive signals from the speech processor and convert them into electric impulses; and 4) an electrode array, which is a group of electrodes that collects the impulses from the stimulator and sends them to different regions of the auditory nerve. In an exemplary embodiment, the cochlear implant may be a small, complex electronic device that can help to provide a sense of sound to a person who is profoundly deaf or severely hard-of-hearing. The implant consists of an external portion that sits behind the ear and a second portion that is surgically placed under the skin.

According to an aspect of the present disclosure, a patient that may qualify for the therapy taught herein can be either: (1) a current user of a cochlear implant or (2) be a candidate for a cochlear implant, but not a current user, i.e. a new cochlear implant user that desires gene therapy treatment in conjunction with a new cochlear implant installation (both done at the same time).

Cochlear implants are designed to mimic the function of a healthy inner ear (or cochlea), They replace the function of damaged sensory hair cells inside the inner ear to help provide clearer sound than what hearing aids can provide. When a person experiences hearing loss or has their hearing impaired significantly, a cochlear implant may be implanted to allow a person to take in external information through their auditory nerve. During sensorineural hearing loss, which means hair cells in a person's inner ear are damaged, the damaged hair cells are no longer capable of sending sounds to their auditory nerve. As alluded to above, a cochlear implant bypasses or skips these damaged hair cells in the inner ear to delivery information directly to the auditory nerve, Studies have shown that certain genes are susceptible to mutation that prematurely damage or deteriorate these hair cells (and/or the spiral ganglion) at birth or sometime later in the person's life. As described above, studies have demonstrated that mutations in the two genes that cause deafness, TMPRSS3 and LoxHD1, may have poor outcomes in cochlear implant results[1]. Specifically, the typical TMPRSS3 mutant patient may have dysfunction in either or both of their spiral ganglion and hair cells. During evaluation of a mouse TMPRSS3 mutant model, it was demonstrated that hair cells degenerated initially and was followed shortly after by the degeneration of spiral ganglion cells[3]. During evaluation of human patients with TMPRSS3 mutations, it was further demonstrated that cochlear implant function declines with age, which suggests that the delayed degeneration of spiral ganglion cells also occurs in the human population[4].

As stated earlier, patients with mutations in TMPRSS3 may not respond to cochlear implantation as well as patients with other mutations (Shearer et al., 2017). This presents the opportunity of targeting TMPRSS3, or other genes such as LOXHD1, using gene therapy techniques to repair these damaged hair cells and/or spiral ganglion cells in combination with cochlear implantation to improve implant outcomes for this disorder. In other words, the cochlear implant may be used to bypass the defective hair cells and directly stimulate the spiral ganglion cells, and, in combination with the implant, gene therapy may be used to fix the damaged hair cells and/or the spiral ganglion cells that have either been destroyed via natural causes and/or genetic defects. It can be appreciated that any commercially available cochlear implant may be utilized by the systems and methods described herein.

It can be appreciated that in some cases genetic disorders may cause defective hair cells and/or spiral ganglion at the time of birth. In some children, however, the genetic mutation that may result in partial or total hearing loss may come at a later stage in life (e.g., adolescence, adulthood, etc.).

Figure 7:
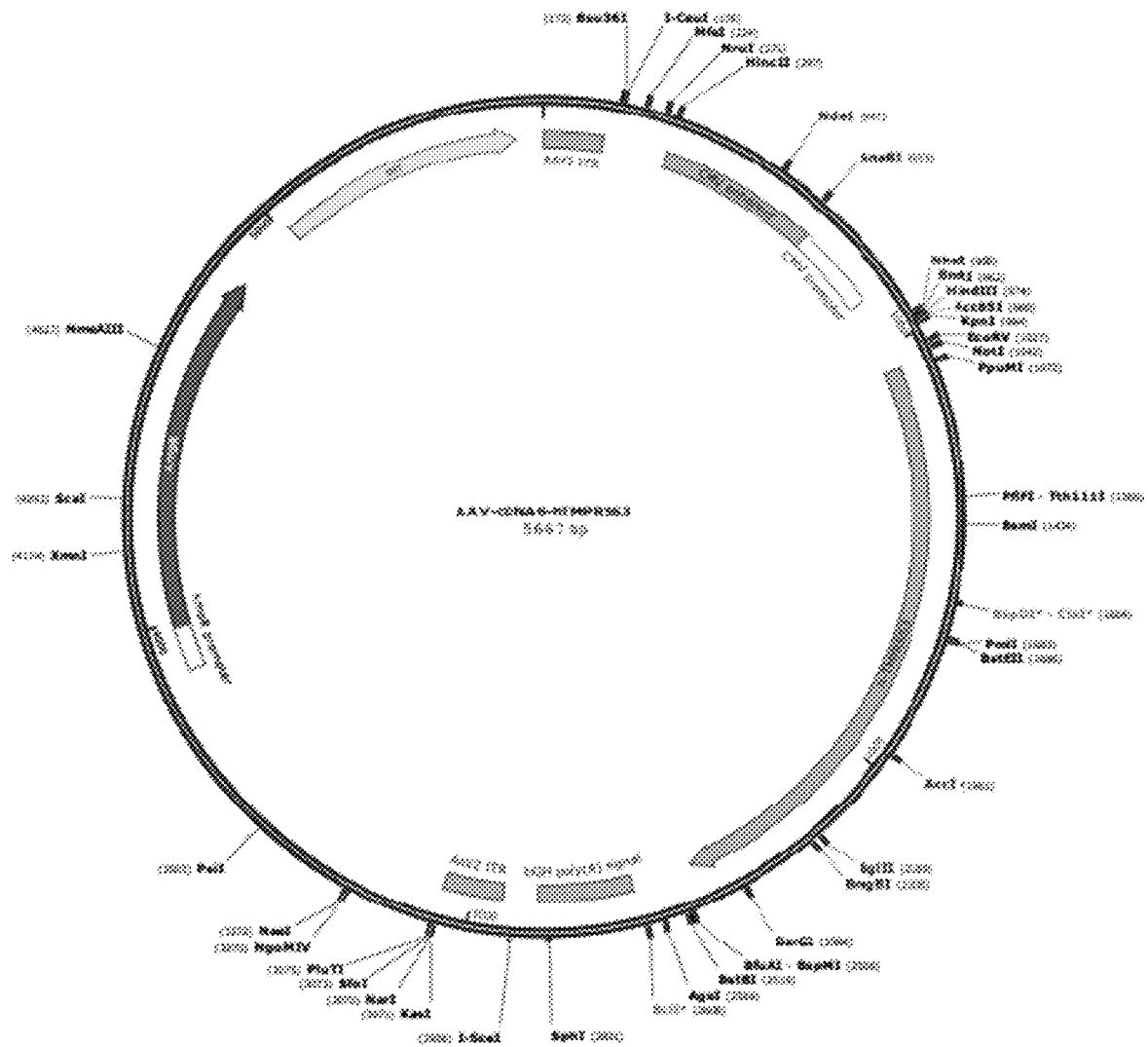
FIG. 7 shows an exemplary TMPRSS3 plasmid map beginning at "ORI" and including an initial "AAV2 ITR" vector, a "CMV enhancer", a "CMV promoter", a "h-TMPRSS3", a "bGH poly(A) signal, and a closing "AAV2 ITR" vector.

Aspects of the present disclosure cover exemplary embodiments regarding gene therapy (e.g., TMPRSS3, LoxHD1, etc.) for treatment and/or repair of these genetically defective cells of the inner ear (e.g., hair cells, spiral ganglion, etc.). FIG. 7 depicts an exemplary plasmid map for a TMPRSS3 vector construct that may be utilized in gene therapy according to aspects taught herein. The plasmid map illustrates a "AAV-cDNA 6-hTMPRSS3" with 5,667 bp. Cochlear implantation, with gene therapy using the "AAV-cDNA 6-hTMPRSS3" plasmid, may be utilized to achieve one or more of the objectives prescribed in this disclosure.

For example, the "AAV-cDNA 6-hTMPRSS3" depicted as FIG. 2 may be used to genetically treat or repair mutations of the TMPRSS3 gene. In doing so, and depending upon the time of the intervention of the gene therapy, the modified TMPRSS3 gene may repair damaged hair cells and/or spiral ganglion caused by mutated and defective genes.

The plasmid map of FIG. 7, in an exemplary embodiment, beginning at "ORI" and including an initial "AAV2 ITR" vector, a "CMV enhancer", a "CMV promoter", a "h-TM-PRSS3", a "bGH poly(A) signal, and a closing "AAV2 ITR" vector. Optionally, an additional therapeutic construct "AmpR promoter' may be used. It can be appreciated that other vectors may be utilized to achieve objectives according to aspects of the present disclosure.

Proof of Concept

Mouse Model:

A TRMPSS mouse model in the CBA/J background was generated. These models when bred with the CBA/J strain established the mutant line. The mutation was a knock in model point mutation. The mutation was c.916G>A (p.Ala306Thr) homozygeous mutation.

TMPRSS3 c.916G>A (p.Ala306Thr), has been identified in more than 10 families from Chinese, German, Dutch, and Korean deaf patients, indicating that this mutation is the main contributor to the DFNB8/DFNB10 phenotype in many ethnicities. (Weegerink et al., 2011; J. Lee et al., 2013; J. Chung et al., 2014; M. Elbracht et al., 2007; Gao X et al., 2017)

Layman Explanation of ABR Test:

The ABR test measures auditory function. The X-axis (Horizontal) lists the Frequencies (Pitch) which are expressed in kilohertz (kh). Numbers to the left of the X-axis are low pitch (like a bass note) as you move to the right, the numbers or pitch get higher (like a flute note). The Y-Axis (Vertical) describes the "Threshold" of hearing or loudness (expressed in decibels or db) i.e. how loud do we have to turn up the volume until the mouse hears.

Figure 6:
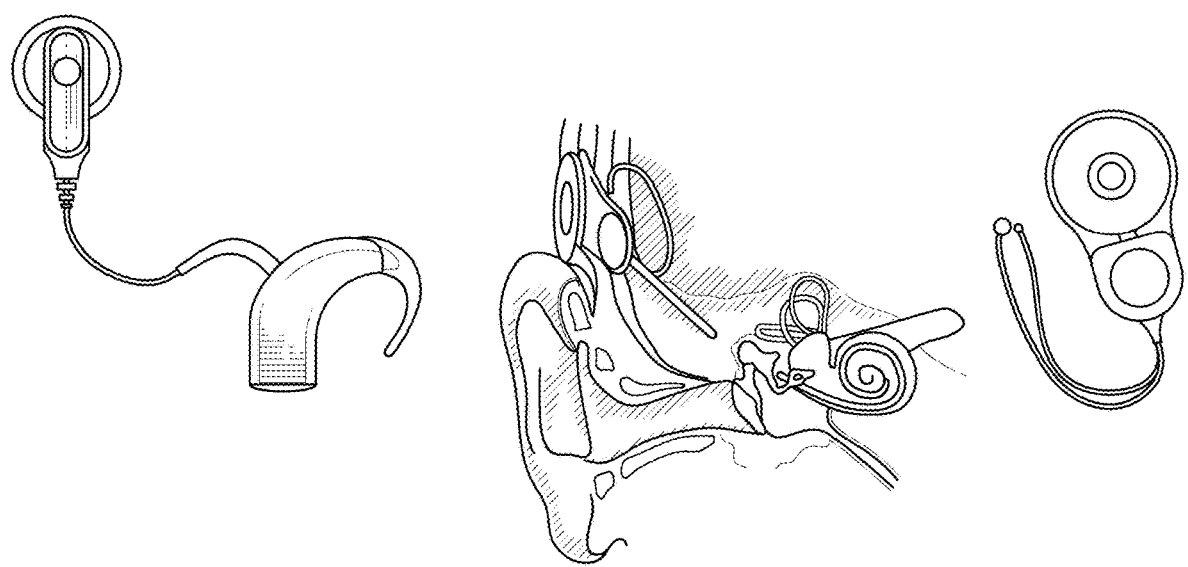
FIG. 6 shows an exemplary cochlear implant and the corresponding anatomy of the inner human, according to an aspect of the present disclosure.
Figure 8:
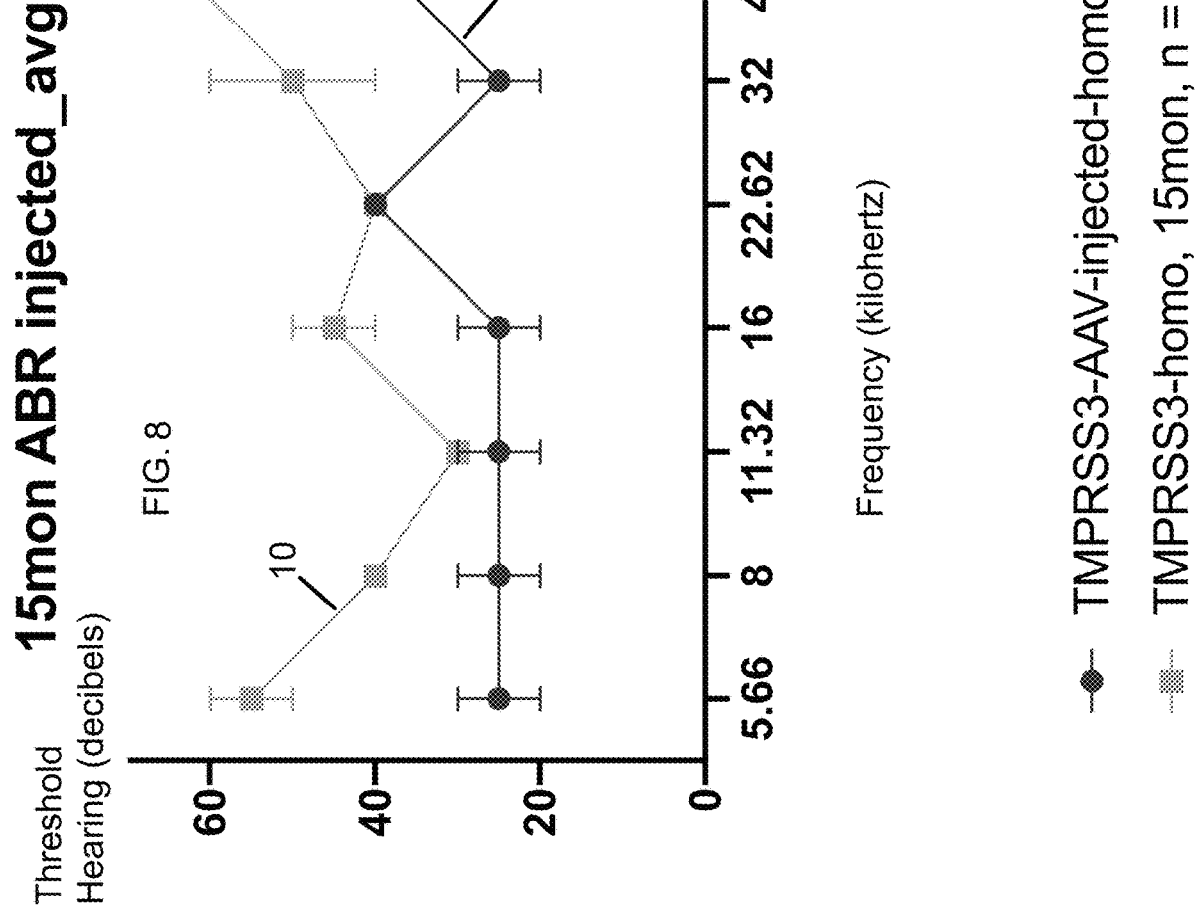
FIG. 8 illustrates proof of concept by graphically comparing hearing recovery of a disease model mouse receiving gene therapy treatment (treated) vs a disease model mouse not receiving treatment (untreated) by way of Auditory Brainstem Response (ABR) testing.

As shown in FIG. 8, the auditory brain response (ABR) test was utilized to measure hearing thresholds at different frequencies for mutant (untreated) mice and mutant experimental (treated) mice. There were 2 mice in the untreated group (10) and 2 mice in the treated group (12). The treated mice (12) had been injected with 1 uL (microliter) of AAV-TMPRSS3 (gene therapy treatment) at the contralateral inner ear. After 1 month (time following injection), the hearing of both treated and un-treated mice were tested using ABR. As shown in FIG. 6, the hearing thresholds for the treated mice (12) were much lower than the hearing thresholds for the control (untreated) mouse (10). Interpretation—The treated mouse (12) hears all frequencies sooner (at a lower volume) than the untreated mouse 10.

Figure 9:
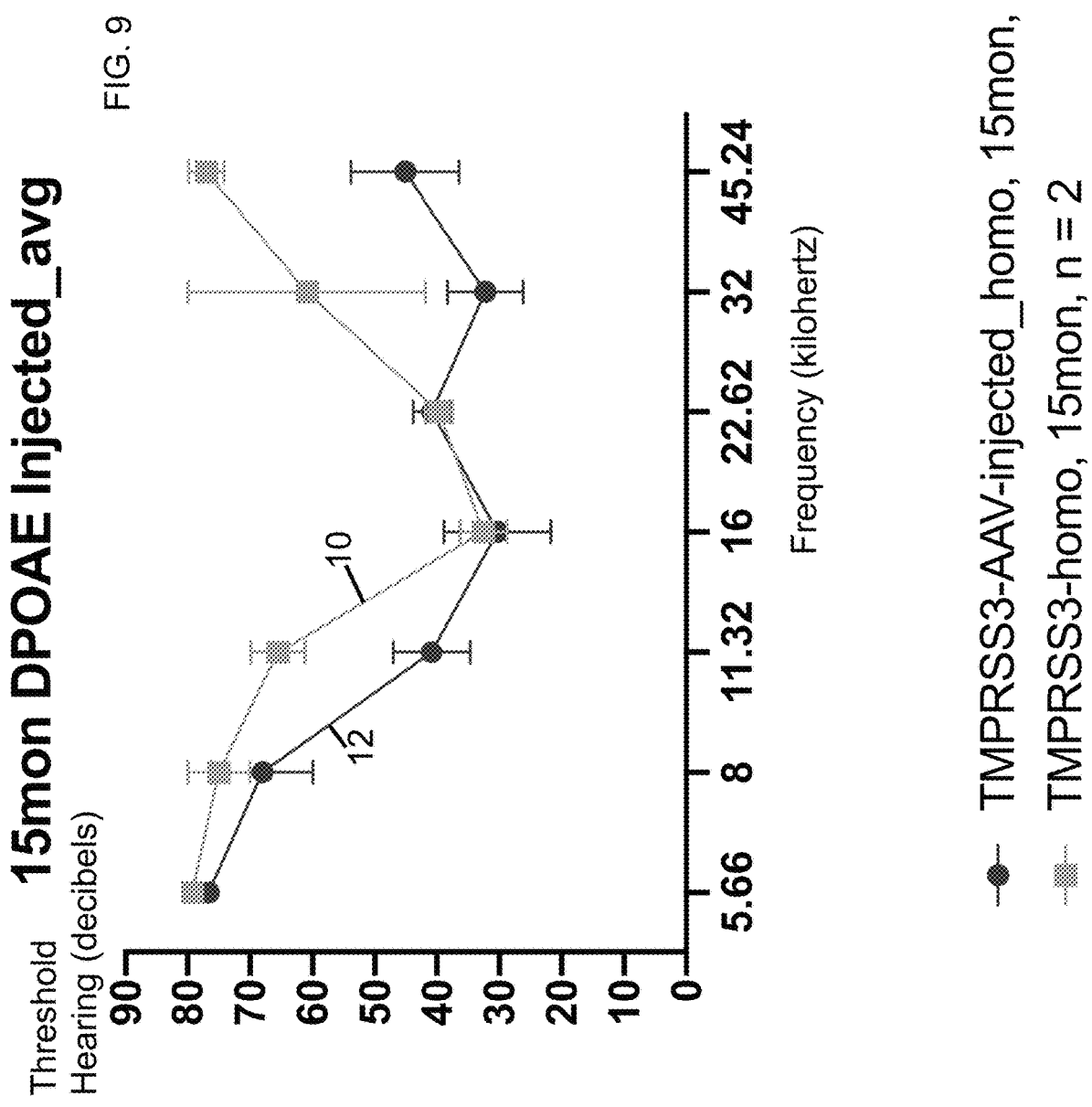
FIG. 9 illustrates proof of concept by graphically comparing hearing recovery of a disease model mouse receiving gene therapy treatment (treated) vs a disease model mouse not receiving treatment (untreated) by way of Distortion Product Otoacoustic Emissions (DPOAE) testing.
Figure 10:
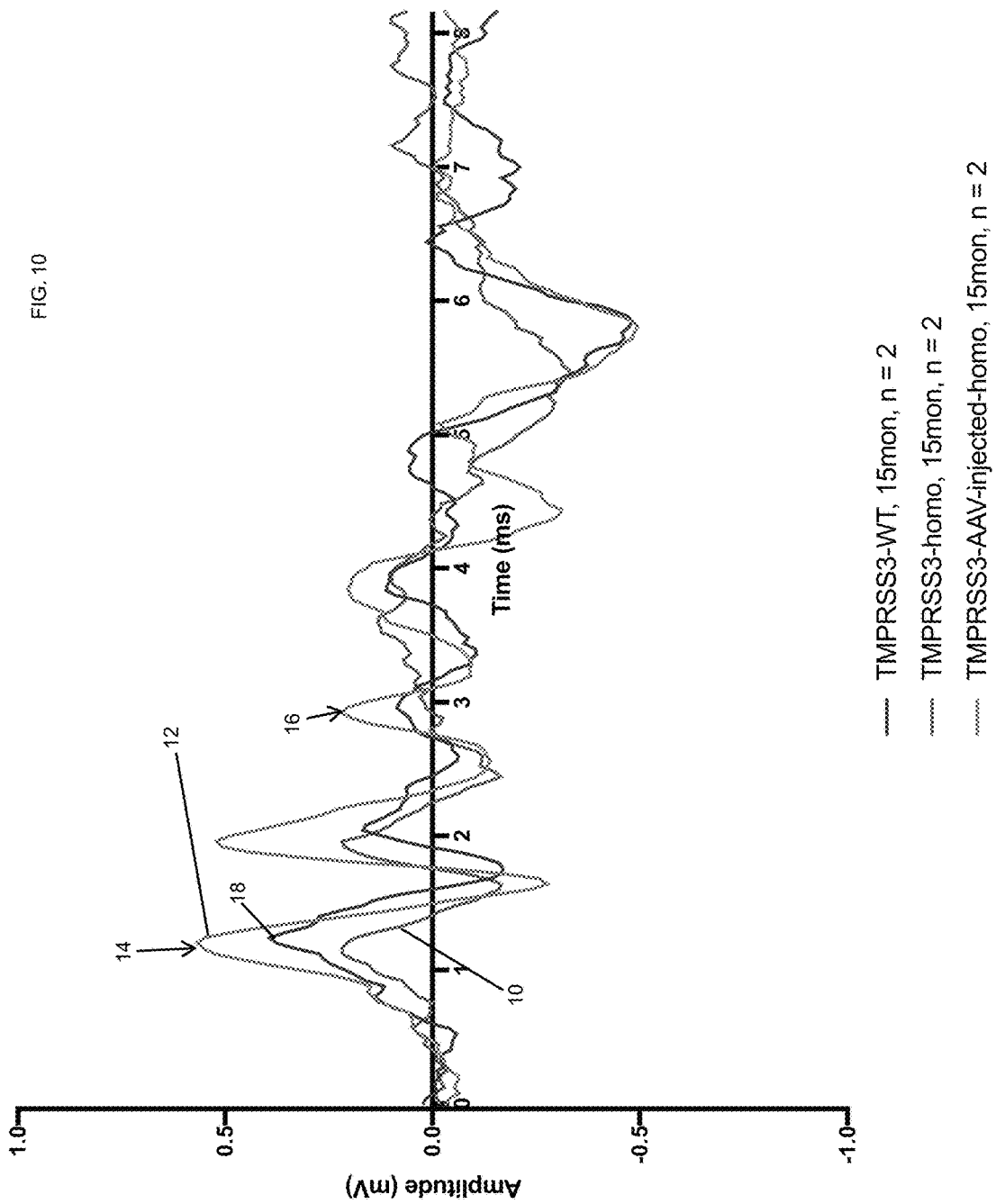
FIG. 10 graphically illustrates proof of concept by graphically comparing auditory neuronal function recovery of a disease model mouse receiving gene therapy treatment (treated) vs a disease model mouse not receiving treatment (untreated) by way of WAVE1 amplitude testing.

Layman Explanation of DPOAE Test:

DPOAE is a measure of outer hair cell (OHC) function. The OHCs control volume of incoming sound (i.e. the ear's volume control knob). In FIG. 9, the X and Y axis are same as in FIG. 8. The X-axis is frequency or pitch and Y-axis is threshold or volume needed to hear.

Turning to FIG. 9, shown is a similar improvement utilizing the distortion product otoacoustic emissions test (DPOAE). DPOAE thresholds were elevated in 15 month old untreated mice (10) while the treated mice (12) DPOAE thresholds were restored to normal levels. Interpretation—the treated mouse (12) required less volume to hear the sound than the untreated mouse (10). The data demonstrates that the OHCs of the treated mouse (12) are returning to normal function.

Layman Explanation of WAVE1 Test:

The WAVE 1 test is an additional measurement provided by the ABR test. Wave 1 amplitudes measure neuronal activities including the synchronous firing of numerous auditory nerve fibers in the spiral ganglion cells. The (horizontal) X-axis measures the response time to a sound stimulus (click) in milliseconds. The Y-Axis (vertical) describes the "Amplitude" or intensity/sensitivity of the auditory nerve's response to the sound stimulus expressed in millivolts (my).

With reference to FIG. 8, shown is the auditory evoked potential as a result of acoustic stimulation, measured in millivolts, as a function of time, measured in milliseconds. The acoustic stimulation was at a sound pressure level (SPL) of 80 dB at 32 kHz. The neural response generates a cycle of waves of which the first wave 14 and the third wave 16 are usually considered most significant. In this experiment, WAVE1 amplitudes were measured in treated mice (12) and in untreated mice both homozygous (10) and wild type (18). The WAVE1 amplitudes of the treated mice (12) were significantly greater than the amplitudes for the untreated mice (10 and 18). Interpretation—The treated mice (12) nerve cells are "firing" with greater intensity and sensitivity than untreated mice (10, 18).

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

REFERENCES

1. Shearer A E, Eppsteiner R W, Frees K, et al. Genetic variants in the peripheral auditory system significantly affect adult cochlear implant performance. Hear Res. 2017; 348:138-142. doi:10.1016/J.HEARES.2017.02.008.
2. Shearer A E, Tejani V D, Brown C J, et al. In Vivo Electrocochleography in Hybrid Cochlear Implant Users Implicates TMPRSS3 in Spiral Ganglion Function. Sci Rep. 2018; 8(1):14165. doi:10.1038/541598-018-32630-9.
3. Fasquelle L, Scott H S, Lenoir M, et al. Tmprss3, a transmembrane serine protease deficient in human DFNB8/10 deafness, is critical for cochlear hair cell survival at the onset of hearing. J Biol Chem. 2011; 286(19):17383-17397. doi:10.1074/jbc.M110.190652.
4. Professor Hubert Lowenheim, Personal Communication.
5. N. J. Weegerink, M. Schraders, J. Oostrik et al., "Genotype-phenotype correlation in DFNB8/10 families with TMPRSS3 mutations," Journal of the Association for Research in Otolaryngology, vol. 12, no. 6, pp. 753-766, 2011.
6. J. Lee, J. I. Baek, J. Y. Choi, U. K. Kim, S. H. Lee, and K. Y. Lee, "Genetic analysis of TMPRSS3 gene in the Korean population with autosomal recessive nonsyndromic hearing loss," Gene, vol. 532, no. 2, pp. 276-280, 2013.
7. J. Chung, S. M. Park, S. O. Chang et al., "A novel mutation of TMPRSS3 related to milder auditory phenotype in Korean postlingual deafness: a possible future implication for a personalized auditory rehabilitation," J Mol med (Berl), vol. 92, no. 6, pp. 651-663, 2014.
8. M. Elbracht, J. Senderek, T. Eggermann et al., "Autosomal recessive postlingual hearing loss (DFNB8): compound heterozygosity for two novel TMPRSS3 mutations in German siblings," Journal of Medical Genetics, vol. 44, no. 6, article e81, 2007.

9. Gao X, Huang S S, Yuan Y Y, et al., "Identification of TMPRSS3 as a Significant Contributor to Autosomal Recessive Hearing Loss in the Chinese Population," Journal of Neural Plast. 2017; 2017:3192090. doi: 10.1155/2017/3192090. Epub 2017 Jun. 13.

10. (Weegerink et al., 2011; J. Lee et al., 2013; J. Chung et al., 2014; M. Elbracht et al., 2007; Gao X et al., 2017)

What is claimed is:

1. A method for treating or preventing hearing loss in a subject in need thereof, comprising the steps of:
   administering to the subject an effective amount of an expression vector to result in TMPRSS3 expression in inner and outer hair cells and spiral ganglion cells, the expression vector comprising
     an initial AAV2 inverted terminating repeat (ITR) sequence,
     an enhancer,
     a nucleic acid sequence having 100% sequence identity to the nucleic acid of SEQ ID NO: 1 or SEQ ID NO: 3,
     a promoter operatively linked to the nucleic acid sequence, wherein the promoter is a human cytomegalovirus (hCMV) promoter,
     a bGH poly(A) signal, and
     a closing AAV2 inverted terminating repeat (ITR) sequence,
   wherein the expression vector is a wildtype AAV2 adeno-associated viral vector; and
   implanting a cochlear implant in the subject.

2. The method of claim 1, wherein the administration of the expression vector is performed prior to the implantation of the cochlear implant.

3. The method of claim 1, wherein the administration of the expression vector is performed subsequent to the implantation of the cochlear implant.

4. The method of claim 1, wherein the administration of the expression vector and the cochlear implant are performed concurrently.

5. The method of claim 1, wherein the expression vector is administered by injection into the inner ear of the subject.

6. The method of claim 5, wherein the injection method is selected from the group consisting of cochleostomy, round window membrane, endolymphatic sac, scala media, canalostomy, scala media via the endolymphatic sac, or any combination thereof.

7. The method of claim 1, wherein the subject has one or more genetic risk factors associated with hearing loss.

8. The method of claim 7, wherein one of the genetic risk factors is selected from the group consisting of a mutation in the TMPRSS3 gene or a mutation in the LOXHD1 gene.

* * * * *

SEQUENCE LISTING

```
<160> NUMBER OF SEQ ID NOS: 4

<210> SEQ ID NO 1
<211> LENGTH: 1419
<212> TYPE: DNA
<213> ORGANISM: Homo sapiens

<400> SEQUENCE: 1
cggatgtcag aggtcctgaa atagtcacca tggggggaaaa tgatccgcct gctgttgaag      60
cccccttctc attccgatcg cttttttggcc ttgatgattt gaaaataagt cctgttgcac     120
cagatgcaga tgctgttgct gcacagatcc tgtcactgct gccattgaag tttttttccaa    180
tcatcgtcat tgggatcatt gcattgatat tagcactggc cattggtctg ggcatccact     240
tcgactgctc agggaagtac agatgtcgct catcctttaa gtgtatcgag ctgatagctc     300
gatgtgacgg agtctcggat tgcaaagacg gggaggacga gtaccgctgt gtccgggtgg     360
gtggtcagaa tgccgtgctc caggtgttca cagctgcttc gtggaagacc atgtgctccg     420
atgactggaa gggtcactac gcaaatgttg cctgtgccca actgggtttc ccaagctatg     480
taagttcaga taacctcaga gtgagctcgc tggagggca gttccgggag gagtttgtgt      540
ccatcgatca cctcttgcca gatgacaagg tgactgcatt acaccactca gtatatgtga     600
gggagggatg tgcctctggc cacgtggtta ccttgcagtg cacagcctgt ggtcatagaa     660
ggggctacag ctcacgcatc gtgggtggaa acatgtcctt gctctcgcag tggccctggc     720
aggccagcct tcagttccag ggctaccacc tgtgcggggg ctctgtcatc acgcccctgt     780
ggatcatcac tgctgcacac tgtgtttatg acttgtacct ccccaagtca tggaccatcc     840
aggtgggtct agtttccctg ttggacaatc cagccccatc ccacttggtg gagaagattg     900
tctaccacag caagtacaag ccaaagaggc tgggcaatga catcgcccctt atgaagctgg    960
ccgggccact cacgttcaat gaaatgatcc agcctgtgtg cctgcccaac tctgaagaga   1020
acttccccga tggaaagtg tgctggacgt caggatgggg ggccacagag gatggagcag    1080
gtgacgcctc ccctgtcctg aaccacgcgg ccgtcccttt gatttccaac aagatctgca   1140
accacaggga cgtgtacggt ggcatcatct ccccctccat gctctgcgcg ggctacctga   1200
cgggtggcgt ggacagctgc cagggggaca gcggggggcc cctggtgtgt caagagagga   1260
ggctgtggaa gttagtggga gcgaccagct ttggcatcgg ctgcgcagag gtgaacaagc   1320
ctggggtgta cacccgtgtc acctccttcc tggactggat ccacgagcag atggagagag   1380
acctaaaaac ctgaaaagga aggggacaag tagccacct                           1419

<210> SEQ ID NO 2
<211> LENGTH: 454
<212> TYPE: PRT
<213> ORGANISM: Homo sapiens

<400> SEQUENCE: 2

Met Gly Glu Asn Asp Pro Pro Ala Val Glu Ala Pro Phe Ser Phe Arg
1               5                   10                  15

Ser Leu Phe Gly Leu Asp Asp Leu Lys Ile Ser Pro Val Ala Pro Asp
            20                  25                  30
```

```
Ala Asp Ala Val Ala Ala Gln Ile Leu Ser Leu Leu Pro Leu Lys Phe
             35                  40                  45

Phe Pro Ile Ile Val Ile Gly Ile Ile Ala Leu Ile Leu Ala Leu Ala
 50                  55                  60

Ile Gly Leu Gly Ile His Phe Asp Cys Ser Gly Lys Tyr Arg Cys Arg
 65                  70                  75                  80

Ser Ser Phe Lys Cys Ile Glu Leu Ile Ala Arg Cys Asp Gly Val Ser
                 85                  90                  95

Asp Cys Lys Asp Gly Glu Asp Glu Tyr Arg Cys Val Arg Val Gly Gly
             100                 105                 110

Gln Asn Ala Val Leu Gln Val Phe Thr Ala Ala Ser Trp Lys Thr Met
             115                 120                 125

Cys Ser Asp Asp Trp Lys Gly His Tyr Ala Asn Val Ala Cys Ala Gln
             130                 135                 140

Leu Gly Phe Pro Ser Tyr Val Ser Ser Asp Asn Leu Arg Val Ser Ser
145                 150                 155                 160

Leu Glu Gly Gln Phe Arg Glu Glu Phe Val Ser Ile Asp His Leu Leu
                 165                 170                 175

Pro Asp Asp Lys Val Thr Ala Leu His His Ser Val Tyr Val Arg Glu
             180                 185                 190

Gly Cys Ala Ser Gly His Val Val Thr Leu Gln Cys Thr Ala Cys Gly
             195                 200                 205

His Arg Arg Gly Tyr Ser Ser Arg Ile Val Gly Gly Asn Met Ser Leu
             210                 215                 220

Leu Ser Gln Trp Pro Trp Gln Ala Ser Leu Gln Phe Gln Gly Tyr His
225                 230                 235                 240

Leu Cys Gly Gly Ser Val Ile Thr Pro Leu Trp Ile Ile Thr Ala Ala
                 245                 250                 255

His Cys Val Tyr Asp Leu Tyr Leu Pro Lys Ser Trp Thr Ile Gln Val
             260                 265                 270

Gly Leu Val Ser Leu Leu Asp Asn Pro Ala Pro Ser His Leu Val Glu
             275                 280                 285

Lys Ile Val Tyr His Ser Lys Tyr Lys Pro Lys Arg Leu Gly Asn Asp
             290                 295                 300

Ile Ala Leu Met Lys Leu Ala Gly Pro Leu Thr Phe Asn Glu Met Ile
305                 310                 315                 320

Gln Pro Val Cys Leu Pro Asn Ser Glu Glu Asn Phe Pro Asp Gly Lys
                 325                 330                 335

Val Cys Trp Thr Ser Gly Trp Gly Ala Thr Glu Asp Gly Ala Gly Asp
             340                 345                 350

Ala Ser Pro Val Leu Asn His Ala Ala Val Pro Leu Ile Ser Asn Lys
             355                 360                 365

Ile Cys Asn His Arg Asp Val Tyr Gly Gly Ile Ile Ser Pro Ser Met
370                 375                 380

Leu Cys Ala Gly Tyr Leu Thr Gly Gly Val Asp Ser Cys Gln Gly Asp
385                 390                 395                 400

Ser Gly Gly Pro Leu Val Cys Gln Glu Arg Arg Leu Trp Lys Leu Val
                 405                 410                 415

Gly Ala Thr Ser Phe Gly Ile Gly Cys Ala Glu Val Asn Lys Pro Gly
             420                 425                 430

Val Tyr Thr Arg Val Thr Ser Phe Leu Asp Trp Ile His Glu Gln Met
             435                 440                 445

Glu Arg Asp Leu Lys Thr
```

<210> SEQ ID NO 3
<211> LENGTH: 1826
<212> TYPE: DNA
<213> ORGANISM: Homo sapiens

<400> SEQUENCE: 3

| | | | | | | |
|---|---|---|---|---|---|---|
| gtagaaccga | ggtgggggct | tggtgaaggc | acaccaggaa | gagcaggctg | cgcctcaccc | 60 |
| tccagtggag | acagagggca | gacattctct | ttggagcaca | cctcaggcta | aatggcaaaa | 120 |
| ccccaatctc | aagtgaactt | catggaacta | ggggattgtc | tcacttctcc | agtggattga | 180 |
| ggcagtgctc | cctctgttct | ctatgaaatg | acggtgtgga | caggggatgt | ggttggcggg | 240 |
| ggcactgact | ccaacatctt | catgaccctc | tacggcatca | acgggagcac | agaggagatg | 300 |
| cagctggaca | aaagaaagc | caggtttgag | cgggagcaga | acgacacctt | catcatggag | 360 |
| atcctagaca | ttgctccatt | caccaagatg | cggatccgga | ttgatggcct | gggcagtcgg | 420 |
| ccggagtggt | tcctggagag | gatcctactg | aagaacatga | acactggaga | cctgaccatg | 480 |
| ttctactatg | gagactggct | gtcccagcgg | aagggcaaga | agaccctggt | gtgtgaaatg | 540 |
| tgtgccgtta | tcgatgagga | agaaatgatg | gagtggacct | cctacaccgt | cgcagttaag | 600 |
| accagcgaca | tcctgggagc | aggcactgat | gccaacgtgt | tcatcatcat | cttcggggag | 660 |
| aacggggata | gtgggacact | ggccctgaag | cagtcggcaa | actggaacaa | gtttgagcgg | 720 |
| aacaacacgg | acacattcaa | cttccctgac | atgctgagct | gggccaccct | ctgcaagctg | 780 |
| agggtctggc | acgacaacaa | agggatattt | cctggctggc | atctgagcta | tgtcgatgtg | 840 |
| aaggacaact | cccgcgacga | gaccttccac | ttccagtgtg | actgctggct | ctccaagagt | 900 |
| gagggtgacg | gcagacggt | ccgcgacttt | gcctgtgcca | caacaagat | ctgtgatgag | 960 |
| ctggaagaga | ccacctacga | gatcgtcata | gaaacgggca | acggaggcga | aaccagggag | 1020 |
| aacgtctggc | tcatcctgga | gggcaggaag | aaccgatcca | aagagtttct | catggaaaat | 1080 |
| tcttctaggc | agcgggcctt | taggaagggg | accacagaca | cgtttgagtt | tgacagcatc | 1140 |
| tacttggggg | acattgcctc | cctctgtgtg | ggccaccttg | ccagggaaga | ccggtttatc | 1200 |
| cccaagagag | aacttgcctg | gcatgtcaag | accatcacca | tcaccgagat | ggagtacggc | 1260 |
| aatgtgtacc | tctttaactg | tgactgcctc | atcccctca | agaggaagag | gaagtacttc | 1320 |
| aaggtattcg | aggttaccaa | gacgacagag | agctttgcca | gcaaggtcca | gagcctggtg | 1380 |
| cccgtcaagt | acgaagtcat | cgtgacaaca | ggctatgagc | caggggcagg | cactgatgcc | 1440 |
| aacgtcttcg | tgaccatctt | tggggccaac | ggagacacag | gcaagcggga | gctgaagcag | 1500 |
| aaaatgcgca | acctcttcga | gcggggcagc | acagaccgct | tcttcctgga | gacgctggag | 1560 |
| ctgggtgagc | tgcgcaagta | gtgaccaggc | tgggacttgc | tgcagagtgt | ggatgagaaa | 1620 |
| ttgagtcttc | acccagggga | tagaagtgga | gaagcagagg | ccatcaagat | ggtgtatttt | 1680 |
| aagcaaaaac | taattaacac | ttttccccaa | aaaagctagg | ctaattaaat | tattaccaac | 1740 |
| catatcctat | aaagaactca | tcttagcatc | tgcttgctaa | gaagtgtata | cttttcccca | 1800 |
| gtttcaataa | acccagtggc | aagtgg | | | | 1826 |

<210> SEQ ID NO 4
<211> LENGTH: 1114
<212> TYPE: PRT
<213> ORGANISM: Homo sapiens

<400> SEQUENCE: 4

```
Met Asn Asn Glu Ile Thr Tyr Tyr Phe Pro Cys Gln Arg Trp Leu Ala
1               5                   10                  15
Val Glu Glu Asp Asp Gly Gln Leu Ser Arg Glu Leu Leu Pro Val Asp
                20                  25                  30
Glu Ser Tyr Val Leu Pro Gln Ser Glu Glu Gly Arg Gly Gly Gly Asp
            35                  40                  45
Asn Asn Pro Leu Asp Asn Leu Ala Leu Glu Gln Lys Asp Lys Ser Thr
        50                  55                  60
Thr Phe Ser Val Thr Ile Lys Thr Gly Val Lys Lys Asn Ala Gly Thr
65                      70                  75                  80
Asp Ala Asn Val Phe Ile Thr Leu Phe Gly Thr Gln Asp Thr Gly Thr
                    85                  90                  95
Met Thr Leu Leu Lys Ser Ser Lys Thr Asn Ser Asp Lys Phe Glu Arg
                100                 105                 110
Asp Ser Ile Glu Ile Phe Thr Val Glu Thr Leu Asp Leu Gly Asp Leu
            115                 120                 125
Trp Lys Val Arg Leu Gly His Asp Asn Thr Gly Lys Ala Pro Gly Trp
        130                 135                 140
Phe Val Asp Trp Val Glu Val Asp Ala Pro Ser Leu Gly Lys Cys Met
145                 150                 155                 160
Thr Phe Pro Cys Gly Arg Trp Leu Ala Lys Asn Glu Asp Asp Gly Ser
                165                 170                 175
Ile Ile Arg Asp Leu Phe His Ala Glu Leu Gln Thr Arg Leu Tyr Thr
            180                 185                 190
Pro Phe Val Pro Tyr Glu Ile Thr Leu Tyr Thr Ser Asp Val Phe Ala
        195                 200                 205
Ala Gly Thr Asp Ala Asn Ile Phe Ile Ile Tyr Gly Cys Asp Ala
        210                 215                 220
Val Cys Thr Gln Gln Lys Tyr Leu Cys Thr Asn Lys Arg Glu Gln Lys
225                 230                 235                 240
Gln Phe Phe Glu Arg Lys Ser Ala Ser Arg Phe Ile Val Glu Leu Glu
                245                 250                 255
Asp Val Gly Glu Ile Ile Glu Lys Ile Arg Ile Gly His Asn Asn Thr
            260                 265                 270
Gly Met Asn Pro Gly Trp His Cys Ser His Val Asp Ile Arg Arg Leu
        275                 280                 285
Leu Pro Asp Lys Asp Gly Ala Glu Thr Leu Thr Phe Pro Cys Asp Arg
    290                 295                 300
Trp Leu Ala Thr Ser Glu Asp Lys Lys Thr Ile Arg Glu Leu Val
305                 310                 315                 320
Pro Tyr Asp Ile Phe Thr Glu Lys Tyr Met Lys Asp Gly Ser Leu Arg
                325                 330                 335
Gln Val Tyr Lys Glu Val Glu Pro Leu Asp Ile Val Leu Tyr Ser
            340                 345                 350
Val Gln Ile Phe Thr Gly Asn Ile Pro Gly Ala Gly Thr Asp Ala Lys
        355                 360                 365
Val Tyr Ile Thr Ile Tyr Gly Asp Leu Gly Asp Thr Gly Glu Arg Tyr
    370                 375                 380
Leu Gly Lys Ser Glu Asn Arg Thr Asn Lys Phe Glu Arg Gly Thr Ala
385                 390                 395                 400
Asp Thr Phe Ile Ile Glu Ala Ala Asp Leu Gly Val Ile Tyr Lys Ile
                405                 410                 415
```

```
Lys Leu Arg His Asp Asn Ser Lys Trp Cys Ala Asp Trp Tyr Val Glu
                420                 425                 430
Lys Val Glu Ile Trp Asn Asp Thr Asn Glu Asp Glu Phe Leu Phe Leu
            435                 440                 445
Cys Gly Arg Trp Leu Ser Leu Lys Lys Glu Asp Gly Arg Leu Glu Arg
450                 455                 460
Leu Phe Tyr Glu Lys Glu Tyr Thr Gly Asp Arg Ser Ser Asn Cys Ser
465                 470                 475                 480
Ser Pro Ala Asp Phe Trp Glu Ile Ala Leu Ser Ser Lys Met Ala Asp
                485                 490                 495
Val Asp Ile Ser Thr Val Thr Gly Pro Met Ala Asp Tyr Val Gln Glu
            500                 505                 510
Gly Pro Ile Ile Pro Tyr Tyr Val Ser Val Thr Thr Gly Lys His Lys
        515                 520                 525
Asp Ala Ala Thr Asp Ser Arg Ala Phe Ile Phe Leu Ile Gly Glu Asp
    530                 535                 540
Asp Glu Arg Ser Lys Arg Ile Trp Leu Asp Tyr Pro Arg Gly Lys Arg
545                 550                 555                 560
Gly Phe Ser Arg Gly Ser Val Glu Glu Phe Tyr Val Ala Gly Leu Asp
                565                 570                 575
Val Gly Ile Ile Lys Lys Ile Glu Leu Gly His Asp Gly Ala Ser Pro
            580                 585                 590
Glu Ser Cys Trp Leu Val Glu Leu Cys Leu Ala Val Pro Thr Gln
        595                 600                 605
Gly Thr Lys Tyr Met Leu Asn Cys Asn Cys Trp Leu Ala Lys Asp Arg
    610                 615                 620
Gly Asp Gly Ile Thr Ser Arg Val Phe Asp Leu Leu Asp Ala Met Val
625                 630                 635                 640
Val Asn Ile Gly Val Lys Val Leu Tyr Glu Met Thr Val Trp Thr Gly
                645                 650                 655
Asp Val Val Gly Gly Thr Asp Ser Asn Ile Phe Met Thr Leu Tyr
            660                 665                 670
Gly Ile Asn Gly Ser Thr Glu Glu Met Gln Leu Asp Lys Lys Lys Ala
        675                 680                 685
Arg Phe Glu Arg Glu Gln Asn Asp Thr Phe Ile Met Glu Ile Leu Asp
    690                 695                 700
Ile Ala Pro Phe Thr Lys Met Arg Ile Arg Ile Asp Gly Leu Gly Ser
705                 710                 715                 720
Arg Pro Glu Trp Phe Leu Glu Arg Ile Leu Leu Lys Asn Met Asn Thr
                725                 730                 735
Gly Asp Leu Thr Met Phe Tyr Tyr Gly Asp Trp Leu Ser Gln Arg Lys
            740                 745                 750
Gly Lys Lys Thr Leu Val Cys Glu Met Cys Ala Val Ile Asp Glu Glu
        755                 760                 765
Glu Met Met Glu Trp Thr Ser Tyr Thr Val Ala Val Lys Thr Ser Asp
    770                 775                 780
Ile Leu Gly Ala Gly Thr Asp Ala Asn Val Phe Ile Ile Ile Phe Gly
785                 790                 795                 800
Glu Asn Gly Asp Ser Gly Thr Leu Ala Leu Lys Gln Ser Ala Asn Trp
                805                 810                 815
Asn Lys Phe Glu Arg Asn Asn Thr Asp Thr Phe Asn Phe Pro Asp Met
            820                 825                 830
Leu Ser Leu Gly His Leu Cys Lys Leu Arg Val Trp His Asp Asn Lys
```

-continued

```
                    835                 840                 845
Gly Ile Phe Pro Gly Trp His Leu Ser Tyr Val Asp Val Lys Asp Asn
                850                 855                 860

Ser Arg Asp Glu Thr Phe His Phe Gln Cys Asp Cys Trp Leu Ser Lys
865                 870                 875                 880

Ser Glu Gly Asp Gly Gln Thr Val Arg Asp Phe Ala Cys Ala Asn Asn
                    885                 890                 895

Lys Ile Cys Asp Glu Leu Glu Thr Thr Tyr Glu Ile Val Ile Glu
                900                 905                 910

Thr Gly Asn Gly Gly Glu Thr Arg Glu Asn Val Trp Leu Ile Leu Glu
                915                 920                 925

Gly Arg Lys Asn Arg Ser Lys Glu Phe Leu Met Glu Asn Ser Ser Arg
    930                 935                 940

Gln Arg Ala Phe Arg Lys Gly Thr Thr Asp Thr Phe Glu Phe Asp Ser
945                 950                 955                 960

Ile Tyr Leu Gly Asp Ile Ala Ser Leu Cys Val Gly His Leu Ala Arg
                965                 970                 975

Glu Asp Arg Phe Ile Pro Lys Arg Glu Leu Ala Trp His Val Lys Thr
                980                 985                 990

Ile Thr Ile Thr Glu Met Glu Tyr Gly Asn Val Tyr Phe Phe Asn Cys
        995                 1000                1005

Asp Cys Leu Ile Pro Leu Lys Arg Lys Arg Lys Tyr Phe Lys Val
    1010                1015                1020

Phe Glu Val Thr Lys Thr Thr Glu Ser Phe Ala Ser Lys Val Gln
    1025                1030                1035

Ser Leu Val Pro Val Lys Tyr Glu Val Ile Val Thr Thr Gly Tyr
    1040                1045                1050

Glu Pro Gly Ala Gly Thr Asp Ala Asn Val Phe Val Thr Ile Phe
    1055                1060                1065

Gly Ala Asn Gly Asp Thr Gly Lys Arg Glu Leu Lys Gln Lys Met
    1070                1075                1080

Arg Asn Leu Phe Glu Arg Gly Ser Thr Asp Arg Phe Phe Leu Glu
    1085                1090                1095

Thr Leu Glu Leu Val Val Thr Arg Leu Gly Leu Ala Ala Glu Cys
    1100                1105                1110

Gly
```